(12) United States Patent
Yamauchi et al.

(10) Patent No.: US 12,012,382 B2
(45) Date of Patent: *Jun. 18, 2024

(54) POLYMERIZABLE LIQUID CRYSTAL HAVING A CARBAZOLE CORE

(71) Applicant: ROLIC TECHNOLOGIES AG, Allschwil (CH)

(72) Inventors: Shinnosuke Yamauchi, Amagasaki (JP); Fabien Nekelson, Chiba (JP); Sabrina Chappellet, Village-Neuf (FR)

(73) Assignee: ROLIC TECHNOLOGIES AG, Allschwil (CH)

( * ) Notice: Subject to any disclaimer, the term of this patent is extended or adjusted under 35 U.S.C. 154(b) by 216 days.

This patent is subject to a terminal disclaimer.

(21) Appl. No.: 17/612,300

(22) PCT Filed: Jun. 26, 2020

(86) PCT No.: PCT/EP2020/068076
§ 371 (c)(1),
(2) Date: Nov. 18, 2021

(87) PCT Pub. No.: WO2020/260617
PCT Pub. Date: Dec. 30, 2020

(65) Prior Publication Data
US 2022/0259148 A1  Aug. 18, 2022

(30) Foreign Application Priority Data

Jun. 28, 2019 (EP) ..................................... 19183343
Aug. 28, 2019 (EP) ..................................... 19194035

(51) Int. Cl.
*G02F 1/1333* (2006.01)
*C07D 209/86* (2006.01)
*C09K 19/38* (2006.01)
*G02B 5/30* (2006.01)

(52) U.S. Cl.
CPC ........ *C07D 209/86* (2013.01); *C09K 19/3823* (2013.01); *G02B 5/3016* (2013.01); *C09K 2219/03* (2013.01)

(58) Field of Classification Search
CPC ............ C09K 19/3804; C09K 19/3823; C09K 2019/0444; C09K 2019/0448; G02F 1/1333; G02B 5/3016
See application file for complete search history.

(56) References Cited

U.S. PATENT DOCUMENTS

| | | | |
|---|---|---|---|
| 4,122,027 A | 10/1978 | Cole, Jr. et al. | |
| 4,401,369 A | 8/1983 | Jones | |
| 4,565,424 A | 1/1986 | Huffman et al. | |
| 4,667,020 A | 5/1987 | Etzbach et al. | |
| 5,539,074 A | 7/1996 | Herr et al. | |
| 6,107,427 A | 8/2000 | Herr et al. | |
| 6,201,087 B1 | 3/2001 | Herr et al. | |
| 2002/0061996 A1 | 5/2002 | Buchecker et al. | |
| 2008/0274304 A1 | 11/2008 | Cherkaoui et al. | |
| 2017/0369783 A1 | 12/2017 | Horiguchi et al. | |
| 2022/0259148 A1* | 8/2022 | Yamauchi ............ | G02B 5/3016 |
| 2022/0298418 A1* | 9/2022 | Chappellet ........... | C09K 19/067 |

FOREIGN PATENT DOCUMENTS

| | | |
|---|---|---|
| EP | 2703385 A1 | 3/2014 |
| JP | 2016-128403 A | 7/2016 |
| WO | 2012/147904 A1 | 11/2012 |
| WO | 2016/104317 A1 | 6/2016 |
| WO | 2017/043437 A1 | 3/2017 |

OTHER PUBLICATIONS

International Search Report of PCT/EP2020/068076 dated Jul. 20, 2020 [PCT/ISA/210].
Written Opinion of PCT/EP2020/068076 dated Jul. 20, 2020 [PCT/ISA/237].

* cited by examiner

*Primary Examiner* — Geraldina Visconti
(74) *Attorney, Agent, or Firm* — Sughrue Mion, PLLC

(57) ABSTRACT

The invention relates to novel anisotropic compounds of formula

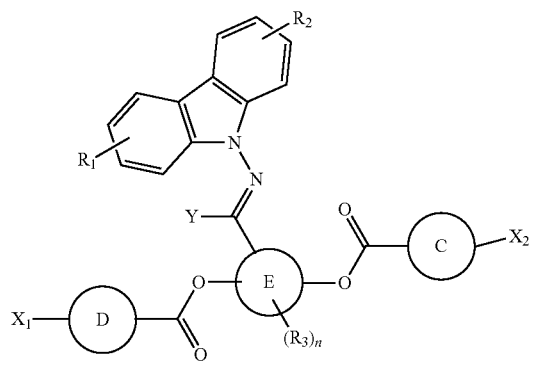

as well as to liquid crystalline mixtures, films and electro-optical devices comprising the compound.

15 Claims, 2 Drawing Sheets

POLYMERIZABLE LIQUID CRYSTAL HAVING A CARBAZOLE CORE

CROSS REFERENCE TO RELATED APPLICATIONS

This application is a National Stage of International Application No. PCT/EP2020/068076 filed on Jun. 26, 2020, claiming priority based on European Patent Application No. 19183343.3 filed on Jun. 28, 2019 and European Patent Application No. 19194035.2 filed on Aug. 28, 2019.

BACKGROUND OF THE INVENTION

The present invention relates to novel polymerizable anisotropic Liquid Crystals (LCPs) compounds having a carbazole core, to compositions comprising such LCPs compounds and to optical films comprising such LCPs compounds or compositions. Optical films comprising the LCPs according to the present invention shown reverse retardation pattern of polarized light over a wide wavelength band. Finally, the present invention relates to optically anisotropic articles comprising such LCPs compounds or comprising optical films comprising such LCPs compounds such as, e.g. flat displays, TVs, smartphones, tablets.

Optical films prepared from curable LCPs compounds (LCP films) are well known to a skilled person and are used in the preparation of optical devices. Examples of optical films are retardation films or polarizers. Retardation films are a type of optical elements which change the polarization state of light passing through the same. When light passes through a retardation film, the polarization direction of the light changes because of the birefringence and the thickness of the film. Quarter-wave retardation plates convert linearly polarized light into circularly polarized light, and half-wave retardation plates convert the plane of vibration of linearly polarized light by 90°. Such retardation films can achieve conversion of specific monochromatic light so that λ/4 or λ/2 retardation occurs. However, the known retardation films have the drawback that the polarized light that passes through is converted into coloured polarized light. Further, a polarization state distribution corresponding to each wavelength occurs for polarized white light. Therefore, it is impossible to achieve accurate λ/4 or λ/2 retardation over the entire wavelength band. To improve such drawbacks, there is the need to develop retarder films having a wavelength dispersion which is higher in the long wavelength than in the short wavelength. Another issue in preparation of retardation films, also known as retarders, is to prepare high performing films at a small charge of materials.

There is, therefore, a need for new LCP compounds that may be used in the preparation of an optical film as described above, which significantly reduces the aforementioned disadvantages. The present invention addresses that need.

Several anisotropic LCP compounds are already known in the art, but there is still the demand to develop new LCP compounds with improved uniform conversion of polarized light over a wider wavelength. Few examples of such anisotropic LCP compounds are disclosed in WO2012/147904, WO2016/104317, WO2017/043437 and JP2016/128403.

LCP films are generally manufactured by method well-known by the skilled person. This involves coating an organic solution of a cross-linkable LCP or LCP mixture onto a substrate provided with an orientation layer or onto a substrate which has previously been treated by the rubbing technique. Or other aligning techniques for liquid crystals may be used. The organic solvent is subsequently removed to give a well-oriented, solvent-free LCP layer, which in turn is cross-linked to fix the liquid crystalline properties ordered structure. The desired optical performance of such films depends crucially on some physical parameters which the anisotropic LCP material has to fulfil simultaneously. Such properties are a low melting point or a low tendency to crystallise when cooled below melting point (supercooling), good solubility in organic solvents, good miscibility with other LCPs, good aligning properties on orientation layers, and the ability to form an adjustable tilt out of the substrate plane essentially free of tilt domains and disclinations. Tilt domains are regions within the LCP film in which the long axes of the LCP molecules form tilt angles out of the plane of the substrate of the same size but in opposite direction. Disclinations are borderlines of neighbouring tilt domains where LCP molecules of opposite tilt angles are adjacent. These tilt domains and disclinations result in both a disturbance in the uniform appearance of the film and an inhomogeneous optical performance.

SUMMARY OF THE INVENTION

It is a first object of the present invention to provide an anisotropic LCP compound as described by formula (I) and to compositions comprising at least one of said compounds and at least one additive and/or a solvent.

It is a further object of the present invention to provide an optical film comprising at least one of said anisotropic LCP compound and to methods of its preparation, to the use of said optical film as retardation film achieving uniform conversion of polarized light and to devices comprising said optical films and their manufacturing.

DETAILED DESCRIPTION OF THE INVENTION

Figure 1:
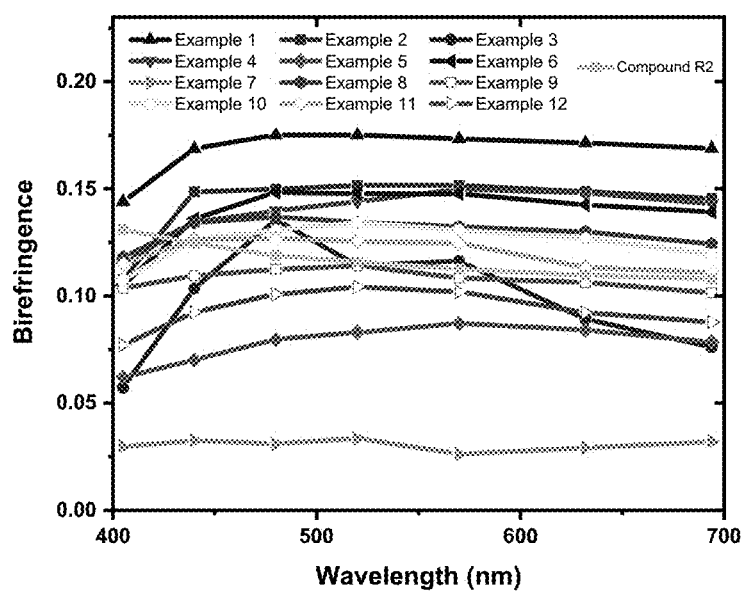
FIG. 1. shows the wavelength dispersion of the Birefringence on rubbed substrates for examples 1 to 13 as compared to comparative examples R2.

The first aspect of the invention provides a liquid crystalline compound of formula (I)

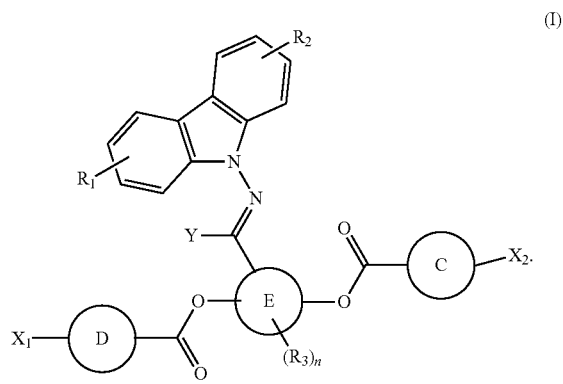

Further, the invention provides LCP mixtures comprising such compounds, LCP networks comprising said compounds or LCP mixture, the use of said compounds, LCP mixtures or LCP networks and optical or electro-optical devices comprising said compounds, LCP mixtures or LCP networks.

In the compounds of formula (I), $R_1$, $R_2$ and $R_3$ are independently from each other selected from the group consisting of hydrogen, $C_1$-$C_{12}$ straight or branched alkyl chain, $C_3$-$C_{12}$ alkenyl, $C_1$-$C_{12}$ alkoxy, $C_3$-$C_{12}$ alkenyloxy, —(CH$_2$)$_m$—C(CH$_3$)$_3$, NO$_2$, CN, COR, —COOR, —OCOR, —CONR'R, —NR'COR, OCOOR, —OCOONR'R, —NR'COOR, —F, —Cl, —CF$_3$ and —OCF$_3$;

in which m is an integer between 0 and 12;

R is selected from the group consisting of hydrogen, an $C_{1-18}$ alkyl group, an $C_{3-18}$ alkenyl group with the double bond at 3-position or higher, —(CH$_2$)$_p$—C—(CF$_3$)$_3$, CN and unsubstituted or substituted phenyl ring, wherein the substituent of the phenyl ring is selected from the group consisting of $C_1$-$C_6$ straight or branched alkyl chain, $C_1$-$C_6$ alkoxy, —C—(CH$_3$)$_3$, halogen, —CF$_3$, NO$_2$, CN, COR''', —COOR''', —OCOR''', —CONR"R''', —NR"COR''', OCOOR''', —OCONR"R''', —NR"COOR''', —F, —Cl, —CF$_3$ and —OCF$_3$;

in which

R" is selected from the group consisting of hydrogen, a lower alkyl group and a lower alkenyl group;

R''' is selected from the group consisting of hydrogen, an $C_{1-18}$ alkyl group and an $C_{3-18}$ alkenyl group with the double bond at 3-position or higher;

p is an integer between 0 and 12;

R' is selected from the group consisting of hydrogen, lower alkyl, lower alkenyl and lower alkoxy;

and in which n is 0, 1, 2 or 3.

Preferably, $R_1$, $R_2$ and $R_3$ are independently from each other selected from the group consisting of hydrogen, lower alkyl, lower alkenyl, lower alkoxy, lower alkenyloxy, —F, and —CF$_3$.

Most preferably, $R_1$, $R_2$ and $R_3$ are independently from each other selected from the group consisting of hydrogen, methyl, methoxy, —F, —C—(CH$_3$)$_3$ and —CF$_3$.

Y is selected from the group consisting of H, or substituted or unsubstituted alkyl group having 1 to 12 carbon atoms.

Rings C and D are independently from each other selected from the group consisting of phenyl, biphenyl, naphthyl, cycloalkyl, preferably cyclohexyl, bicycloalkyl, preferably bicyclohexyl,

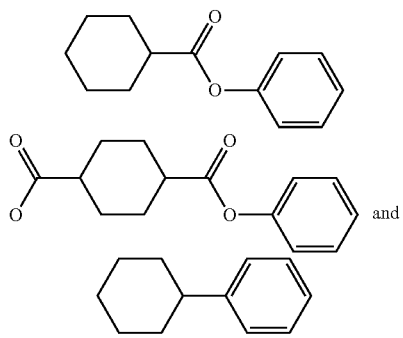

with the proviso that at least one of rings C or D contains an aromatic ring.

Preferably, rings C and D are independently from each other phenyl or cyclohexyl, most preferably both rings C and D are phenyl rings.

Ring E is selected from the group consisting of phenyl, biphenyl and naphthyl.

Preferably, ring E is a phenyl ring.

Substituents $X_1$ and $X_2$ are independently from each other selected from the group consisting of hydrogen, $C_1$-$C_{12}$ substituted or unsubstituted straight or branched alkyl chain, $C_3$-$C_{12}$ substituted or unsubstituted straight chain or branched alkenyl chain and $C_1$-$C_{12}$ alkoxy, wherein one or more carbon atoms may be replaced by —O—, —COO—, —OCO—, —OOC—, —O(CO)O—, —N—, —NR$^a$—, —CON—, wherein R$^a$ is a $C_1$-$C_{12}$ alkyl group; or substituents $X_1$ and $X_2$ independently from each other are represented by the group of formula (II)

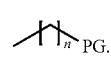

(formula II)

In the group of formula (II), n is an integer between 0 and 24, wherein one or more carbon atoms may be replaced by —O—, —COO—, —OCO—, —OOC—, —O(CO)O—, —N—, —NR$^a$—, —CON—, wherein R$^a$ is a $C_1$-$C_{12}$ alkyl group.

Substituent PG in the group of formula (II) represents a polymerisable group selected from the group consisting of CH$_2$=C(Ph)-, CH$_2$=CW—COO—, CH$_2$=CH—COO-Ph-, CH$_2$=CW—CO—NH—, CH$_2$=CH—O—, CH$_2$=CH—OOC—, Ph-CH=CH—, CH$_2$=CH-Ph-, CH$_2$=CH-Ph-O—, R$^b$-Ph-CH=CH—COO—, R$^b$—OOC—CH=CH-Ph-O— and 2-W-epoxyethyl; in which W represents H, Cl, Ph or a lower alkyl and R$^b$ represents a lower alkyl with the proviso that when R$^b$ is attached to a phenylene group (-Ph-) it may also represent hydrogen or a lower alkoxy. Preferably, PG represents an acrylate or a methacrylate group.

Preferably, substituents $X_1$ and $X_2$ are selected from the group consisting of hydrogen, $C_1$-$C_{12}$ substituted or unsubstituted straight or branched alkyl chain, $C_3$-$C_{12}$ substituted or unsubstituted straight chain or branched alkenyl chain and $C_1$-$C_{12}$ alkoxy when rings C and D are independently from each other cyclohexyl or contain a cyclohexyl.

Preferably, if rings C or D are independently from each other aromatic rings or they contain an aromatic ring, more preferably if C or D are independently from each other phenyl rings or contain phenyl rings, the group of formula (II), is selected from

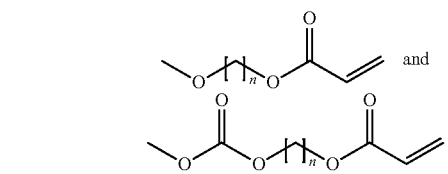

and wherein n has the same meaning as given above, or their corresponding methacrylates.

By the term "lower alkyl" it should be understood to include a $C_{1-6}$ achiral, branched or straight-chained alkyl group. Examples of lower alkyl groups that may be present in the compounds of the invention include methyl, ethyl, propyl, butyl, pentyl, hexyl and the like.

By the term "lower alkenyl" it should be understood to include $C_{3-6}$ achiral, branched or straight-chained alkenyl group in which the double bond is at position 2- or higher. Examples of lower alkenyl groups that may be present in the compounds of the invention include 2-propenyl, 3-butenyl, 3-isopentenyl, 4-pentenyl, 5-hexenyl, 4-isohexenyl and the like.

By the term "lower alkoxy" it should be understood to include $C_{1-6}$ achiral, branched or straight-chained alkoxy group. Examples of lower alkoxy groups that may be present in the compounds of the invention include methoxy, ethoxy, propoxy, butoxy, pentoxy hexoxy and the like.

By the term "lower alkenyloxy" it should be understood to include $C_{3-6}$ achiral, branched or straight-chained alkenyloxy group in which the double bond is at position 2- or higher. Examples of lower alkenyloxy groups that may be present in the compounds of the invention include 2-propenyloxy, 3-butenyloxy, 4-pentenyloxy, 5-hexenyloxy and the like.

The polymerizable anisotropic LCP compounds of the invention may be readily prepared using procedures well known to a skilled person and few non-limiting procedures are provided in the examples.

The starting materials are commercially available or may be readily prepared and are well known to a skilled person.

A polymerizable anisotropic LCP compound material as used within the context of this application shall mean a liquid crystal material, which comprises liquid crystal monomers and/or liquid crystal oligomers and/or liquid crystal polymers and/or cross-linked liquid crystals. In case the liquid crystal material comprises liquid crystal monomers, such monomers may be polymerized, typically after anisotropy has been created in the LCP material, for example due to contact with an aligning layer or by rubbing. Polymerization may be initiated by thermal treatment and/or by exposure to actinic light, which preferably comprises UV-light. An anisotropic LCP-material may comprise only a single type of liquid crystal compound, but may also comprise additional polymerizable and/or non-polymerizable compounds, wherein not all of the compounds have to be liquid crystal compounds. In case of optical films, anisotropic LCP monomers are applied on top of a photo-aligning layer or on top of a rubbed surface. After the alignment information of the photo-aligning layer or of the rubbed surface has been transferred to the LCP monomers, the monomers are polymerized and/or cross-linked in order to solidify the LCP material. It is understood that polymerized or crosslinked polymers according to the present invention may contain only anisotropic LCP compounds of formula (I) alone, and in this case the polymer is a homopolymer, or the polymerized or crosslinked polymers may contain further different monomers, and in this case the polymer is a copolymer. The further different monomer may or may not have LCP properties.

The anisotropic LCP compounds according to the present invention overcome the drawbacks described previously of the LCP compounds of the prior art. Further, the anisotropic LCP compounds according to the present invention have excellent solubility and low temperature processability.

A further object of the present invention relates to a composition comprising the anisotropic LCP compound of formula (I) and at least one solvent and/or additive. The additives can be selected from the following: antioxidants, initiators, such as photoinitiators, accelerators, dyes, inhibitors, activators, fillers, chain transfer inhibitor, pigments, anti-static agents, flame-retardant agents, thickeners, thixotropic agents, surface-active agents, viscosity modifiers, extending oils, plasticizers, tackifiers, catalysts, sensitizers, stabilizers, lubricating agents, dispersing agents, a polymeric binder and/or monomeric compounds which can be converted into the polymeric binder by polymerization, or, in the case of emulsion coatings and printing inks, a dispersion auxiliary, hydrophobing agents, adhesive agents, flow improvers, defoaming agents, deaerators, diluents, auxiliaries, colorants, dyes and pigments, curing inhibitors, a chiral additive, isotropic or anisotropic fluorescent and/or non-fluorescent dyes, in particular dichroic dyes. The solvent that may be used in the preparation of such liquid crystalline compositions include but not limited to acetone, cyclopentanone (CP), cyclohexanone (CH), methyl isobutyl ketone (MIBK), methylethylketone (MEK), N,N-dimethylformamide (DMF), N-methylpyrrolidone (NMP), N-ethylpyrrolidone, N-vinylpyrrolidone, N,N-dimethylacetamide, (AN), tetrahydrofuran (THF), 1,3-dioxolane (DXG), ethylene glycol, dipropylene glycol, butylcarbitol, ethylcarbitol acetate, dipropylene glycol monomethyl ether, ethyl acetate (EA), 1-methoxy-2-propanol acetate (MPA), gamma-butyrolactone (BL), propylene glycol monoacetate, propylene glycol diacetate, dipropylene glycol monomethyl ether, dimethyl sulfoxide (DMSO). Most preferred solvents are cyclopentanone (CP), cyclohexanone (CH), methyl isobutyl ketone (MIBK), methylethylketone (MEK), ethyl acetate (EA), 1-methoxy-2-propanol acetate (MPA), 1,3-dioxolane (DXG), dimethyl sulfoxide (DMSO).

A further preferred object of the present invention relates to a composition comprising the anisotropic LCP compound of formula (I), LCP mixture, and at least one solvent, selected from cyclohexanone, toluene and cyclopentanone; and/or an additive.

A further preferred embodiment of the present invention is a composition, a LCP mixture, comprising the anisotropic compound of formula (I), which preferably has a shelf life stability over more than 3 months with no crystallization.

The present invention relates to an optical film comprising at least one of the anisotropic LCP compounds or compositions according to the present invention. An example of an optical film is a circular polarizer film used as an antireflective film that is produced by combining the optical film according to the present invention with a linear polarizer.

The anisotropic LCP compounds or the composition comprising the anisotropic LCP compounds can be applied on a support. The support may be rigid or flexible and can have any form or shape. In principle it may consist of any material. Preferably, the support comprises plastic, glass or metal or is a silicon wafer. In case the support is flexible, it is preferred that the support is a plastic or metal foil. Preferably, the surface of the support is flat. For some applications the support may comprise topographical surface structures, such as microstructures like micro lenses or micro-prisms, or structures exhibiting abrupt changes of the shape, such as rectangular structures. Preferably, the support is transparent. The support may also have been subjected to a treatment before coating with the anisotropic LCP compound according to the present invention.

The support may be moving during the deposition of the anisotropic LCP compounds or the composition comprising the anisotropic LCP compounds. For example, a layer of the LCP mixture may be produced in a continuous roll to roll process by depositing the material composition onto a moving flexible foil, which is preferably plastic or metallic. The resulting film may then be wound on a roll together with the support foil or the film may be released from the support and is then wound as a free standing film, without the support.

The support may have additional layers, such as photo-aligning layer, organic, dielectric or metallic layers. The layers can have different functions, for example an organic layer can be coated as a primer layer which increases compatibility of the materials to be coated with the support. Metallic layers may be used as electrodes, for example when used in electro-optical devices such as displays, or could have the function as a reflector. The support may also be an optical element or device which has certain functions, such as a substrate for an LCD, which might, for example, comprise thin film transistors, electrodes or color filters. In another example, the support is a device comprising an OLED layer structure. The support could also be a a polarizer, such as a polarizing film or a sheet polarizer, a reflective polarizer, such as the commercially available Vikuity™ DBEF film.

In the context of the present invention, a "photoaligning layer" is made of a material in which anisotropic properties, a photo-orientable substance, can be induced upon exposure to aligning light. In addition the term "photoaligning layer" refers to a layer that has been aligned by exposure to aligning light. For the present invention the induced anisotropy must be as such that it provides alignment capability for the adjacent layer comprising e.g. the anisotropic LCP compounds of formula (I). The term "alignment direction" shall refer to the preferred direction that is induced in the adjacent layer, for example the alignment direction is the direction in which the LCP compounds would be aligned.

Photo-orientable substances incorporate photo-orientable moieties, which are capable of developing a preferred direction upon exposure to aligning light and thus creating anisotropic properties. Such photo-orientable moieties preferably have anisotropic absorption properties. Typically, such moieties exhibit absorption within the wavelength range from 230 to 500 nm. Preferably, the photo-orientable moieties exhibit absorption of light in the wavelength range from 300 to 450 nm, more preferred are moieties, which exhibit absorption in the wavelength range from 310 to 380 nm.

Preferably the photo-orientable moieties have carbon-carbon, carbon-nitrogen, or nitrogen-nitrogen double bonds.

For example, photo-orientable moieties are substituted or un-substituted azo dyes, anthraquinone, coumarin, mericyanine, 2-phenylazothiazole, 2-phenylazobenzthiazole, stilbene, cyanostilbene, fluorostilbene, cinnamonitrile, chalcone, cinnamate, cyanocinnamate, stilbazolium, 1,4-bis(2-phenylethylenyl)benzene, 4,4'-bis(arylazo)stilbenes, perylene, 4,8-diamino-1,5-naphthoquinone dyes, aryloxycarboxylic derivatives, arylester, N-arylamide, polyimide, diaryl ketones, having a ketone moiety or ketone derivative in conjugation with two aromatic rings, such as for example substituted benzophenones, benzophenone imines, phenylhydrazones, and semicarbazones.

Preparation of the anisotropically absorbing materials listed above are well known as shown, e.g. by Hoffman et al., U.S. Pat. No. 4,565,424, Jones et al., in U.S. Pat. No. 4,401,369, Cole, Jr. et al., in U.S. Pat. No. 4,122,027, Etzbach et al., in U.S. Pat. No. 4,667,020, and Shannon et al., in U.S. Pat. No. 5,389,285.

Preferably, the photo-orientable moieties comprise arylazo, poly(arylazo), stilbene, cyanostilbene, cinnamate or chalcone.

A photo-orientable substance may in particular be a monomer, a oligomer or a polymer. The photo-orientable moieties can, for example, be covalently bonded within the main chain or within a side chain of a polymer or oligomer or they may be part of a monomer or other compounds which are not polymerizable. A photo-orientable substance may further be a copolymer comprising different types of photo-orientable moieties or it may be a copolymer comprising side chains with and without photo-orientable moieties.

Polymers denotes for example to polyacrylate, polymethacrylate, polyimide, polyurethane, polyamic acids, polymaleinimide, poly-2-chloroacrylate, poly-2-phenylacrylate; unsubstituted or with $C_1$-$C_6$alkyl substituted poylacrylamide, polymethacyrlamide, poly-2-chloroacrylamide, poly-2-phenylacrylamide, polyether, polyvinylether, polyester, polyvinylester, polystyrene-derivatives, polysiloxane, straight-chain or branched alkyl esters of polyacrylic or polymethacrylic acids; polyphenoxyalkylacrylates, polyphenoxyalkylmethacrylates, polyphenylalkylmethacrylates with alkyl residues of 1-20 carbon atoms; polyacrylnitril, polymethacrylnitril, cycloolephinic polymers, polystyrene, poly-4-methylstyrene or mixtures thereof.

A photo-orientable substance may also comprise photosensitizers, for example, ketocoumarines and benzophenones.

Further, preferred photo-orientable monomers or oligomers or polymers are described in U.S. Pat. Nos. 5,539,074, 6,201,087, 6,107,427, 6,632,909 and 7,959,990.

Alignment of the LCP can be achieved by any other known means for aligning liquid crystals. For example, the support may have an aligning surface, which shall mean that the surface has the capability to align liquid crystals. The support may already provide the alignment without further treatment. For example, if a plastic substrate is used as a support, it may provide alignment on the surface due to the manufacturing method, for example extrusion or stretching of the substrate. It is also possible to brush or rub the support or imprint a directional microstructure to generate alignment capability.

The steps of polymerizing the LCP compounds and exposure to aligning light may be in any sequence. Polymerization may be initiated before or after exposure to aligning light. Or polymerization and exposure may occur simultaneously.

A further embodiment of the present invention relates to a process for manufacturing an optical film comprising an anisotropic compound of formula (I), a LCP mixture or a LCP network according to the present invention, by exposure to aligning light, preferably by an energy of <·200 mJ, more preferably of <150 mJ and more preferably <100 mJ, most preferably <70 mJ.

The LCP mixture may be applied to the support by any suitable method like, extruding, casting, molding, 2D- or 3D-printing or coating. Suitable coating methods are, for example: spin-coating, blade coating, knife coating, kiss roll coating, die coating, dipping, brushing, casting with a bar, roller-coating, flow-coating, wire-coating, spray-coating, dip-coating, curtain-coating, air knife coating, reverse roll coating, gravure coating, metering rod (Meyer bar) coating, slot die (Extrusion) coating, roller coating, flexo coating. Suitable printing methods include: silk screen printing, relief printing such as flexographic printing, jet printing, intaglio printing such as direct gravure printing or offset gravure printing, lithographic printing such as offset printing, or stencil printing such as screen printing.

A further embodiment of the present invention is an optical film comprising an anisotropic compound of formula (I), or the LCP mixture, or LCP network according to the present invention. Preferably, the optical film comprises the aligned anisotropic compound of formula (I), or the LCP mixture, or LCP network. More preferred the alignment quality is uniform with no tilt domains.

In addition, preferred are optical films which have a high contrast ratio in the range of 500-1500 and more preferably in the range of 1500-3000 and most especially in >3000.

Further preferred are optical films comprising LCPs according to the present invention which show reverse retardation pattern of polarized light over a wide wavelength band. The optical films according to the present invention have preferably birefringence with reverse wavelength dispersion: $Re_{450}/Re_{550}$ is below 1.0, preferably $R_{450}/Re_{550}$ is <0.88 and more preferably <0.85; whereas $Re_{650}/Re_{550}$ is above 1.0, preferably $Re_{650}/Re_{550}$ is >1.01 and more preferably of ≥1.03. (The $Re_{450}$ represents the retardation of the film at a wavelength of 450 nm, $Re_{550}$ the retardation of the film at a wavelength of 550 nm and $Re_{650}$ the retardation of the film at a wavelength of 650 nm).

The invention will now be described with reference to the following non-limiting examples. These examples are provided by way of illustration only. Variations on these examples falling within the scope of the invention will be apparent to a skilled person.

EXAMPLES

The following examples are provided to illustrate further and to facilitate understanding of the present invention and are not in any way intended to limit the invention.

Example 1

Synthesis of Compound 1

Synthesis of [3-formyl-4-[4-(6-prop-2-enoyloxy-hexoxy)benzoyl]oxy-phenyl] 4-(6-prop-2-enoyloxy-hexoxy)benzoate Oxalyl chloride (2.5 mL, 29 mmol) was added dropwise to a solution of 4-(6-acryloyloxy-hex-1-yloxy)benzoic acid (6.98 g, 24 mmol) in 48 mL of anhydrous toluene, 4 mg of 4-methoxyphenol and 1 mL of anhydrous DMF at 45° C. After 2 h, the reaction mixture was cooled down to 0° C. and added dropwise at 0-5° C. to a solution of 2,5-dihydroxybenzaldehyde (1.5 g, 11 mmol) in 40 mL of anhydrous DMA and N,N-dimethylcyclohexylamine (7.8 g, 52 mmol). The reaction mixture was stirred at ambient temperature overnight. The orange solution was quenched by addition of 15 mL of water, extracted with dichloromethane and successively washed with water, brine, dried over sodium sulfate and concentrated under vacuo. The title compound was obtained as a white solid (4.19 g, 56%) after recrystallization from dichloromethane/methanol.

$^1$H-NMR (400 MHz, DMSO-$d_6$) δ 10.04 (s, 1H), 8.08 (m, 4H), 7.82 (d, 1H), 7.71 (dd, 1H), 7.54 (d, 1H), 7.10 (m, 4H), 6.26 (d, 1H), 6.15 (dd, 1H), 5.90 (d, 1H), 4.09 (m, 8H), 1.72 (m, 4H), 1.60 (m, 4H), 1.39 (m, 8H). MALDI-TOF (CHCA) 709.27 (M$^+$+Na).

Synthesis of 9-nitrosocarbazole

A solution of sodium nitrite (1.65 g, 24 mmol) in 24 mL of deionized water was added dropwise to a suspension of carbazole (2 g, 12 mmol) and 50% aqueous solution of sulfuric acid (6 mL) in 24 mL of diethyl ether. The yellow-green solution was stirred for 1 h at room temperature under nitrogen atmosphere. The reaction mixture was extracted with diethyl ether, dried over sodium sulfate and concentrated under reduced pressure to yield 2.35 g of the title compound as a solid which was used in the next step without further purification Synthesis of 9-aminocarbazole A solution of 9-nitrosocarbazole (2.35 g, 12 mmol) in anhydrous diethyl ether (20 mL) was added dropwise to a suspension of lithium aluminum hydride (1.13 g, 24 mmol) and 30 mL of anhydrous diethyl ether at 0° C. The grey suspension was allowed to warm to room temperature for 1 h. The excess of hydride was quenched by sequential addition of 10 mL of ethyl acetate and water (10 mL). The reaction mixture was extracted in ethyl acetate, washed with Rochelle's salt, water, brine and dried over sodium sulfate. The brown solid obtained after solvent removal was further purified by flash column chromatography over silica gel using a 1:1 mixture of hexane/dichloromethane. The title compound was obtained as a pale pink solid (1.55 g, 71%).

$^1$H-NMR (400 MHz, DMSO-$d_6$) δ 8.07 (d, 2H), 7.55 (d, 2H), 7.40 (t, 2H), 7.13 (t, 2H), 5.79 (s, 2H)

Synthesis of Benzoic acid 4-[[(6-(acryloxy)hexyl)oxy]benzoyl]oxy]-2-[((1-E)-(9H-carbazol)imino)methyl]-1,4-phenylene] ester (±) 10-Camphorsulfonic acid (23 mg, 0.1 mmol) was added to a solution of [3-formyl-4-[4-(6-prop-2-enoyloxy-hexoxy)benzoyl]oxy-phenyl] 4-(6-prop-2-enoyloxyhexoxy) benzoate (0.67 g, 1.0 mmol) and 9-aminocarbazole (0.21 g, 1.2 mmol) in 10 mL of tetrahydrofuran under an atmosphere of nitrogen. The resulting brown solution was stirred for 2 h at ambient temperature. After completion of the reaction, the reaction mixture was quenched with a 5% aqueous solution of sodium bicarbonate and extracted twice with ethyl acetate. The organic phase was successively washed with water, brine, dried over anhydrous sodium sulfate and the solvent was removed under reduced pressure. The title compound as a pink solid (0.82 g, 99%) was obtained after recrystallization from dichloromethane/methanol.

$^1$H-NMR (400 MHz, DMSO-$d_6$) δ 9.18 (s, 1H), 8.21 (d, 2H), 8.13 (m, 5H), 7.72 (d, 2H), 7.50 (m, 2H), 7.26 (m, 4H), 7.13 (m, 4H), 6.31 (dt, 2H), 6.13 (dddd, 2H), 5.89 (m, 2H), 4.09 (m, 8H), 1.75 (m, 4H), 1.63 (m, 4H), 1.41 (m, 8H). MALDI-TOF (CHCA) 873.32 (M$^+$+Na).

Example 2

Synthesis of Compound 2

Synthesis of 9-amino-3-methylcarbazole

To a suspension of 3-methylcarbazole (4.8 g, 26.5 mmol) and potassium hydroxide (11.9 g, 212 mmol) in dry DMF (53 mL), solution of Hydroxylamine-O-sulfonic acid (HOSA) (5.99 g, 53 mmol) in dry DMF (106 mL) was added dropwise for 65 min at 0° C. After addition, the reaction mixture was quenched with water and extracted with ethyl acetate/hexane=3/1. The organic phase was successively washed with water, brine, dried over anhydrous sodium sulfate and the solvent was removed under reduced pressure to give the title compound as a beige solid (5.1 g, 98%).

$^1$H-NMR (400 MHz, DMSO-$d_6$) δ 8.04 (d, J=7.8 Hz, 1H), 7.88 (s, 1H), 7.54 (d, J=8.2 Hz, 1H), 7.47 (d, J=8.2 Hz, 1H), 7.41 (td, J=7.7, 1.1 Hz, 1H), 7.26 (dd, J=8.2, 1.4 Hz, 1H), 7.12 (t, J=7.5 Hz, 1H), 5.76 (s, 2H), 2.46 (s, 3H).

Synthesis of Benzoic acid 4-[[(6-(acryloxy)hexyl)oxy]benzoyl]oxy]-2-[((1-E)-(3-methyl-9H-carbazol)imino)methyl]-1,4-phenylene] ester (±) 10-Camphorsulfonic acid (18.6 mg, 0.08 mmol) was added to a solution of [3-formyl-4-[4-(6-prop-2-enoyloxyhexoxy)benzoyl]oxy-phenyl] 4-(6-prop-2-enoyloxyhexoxy)benzoate described in example 1 (0.57 g, 0.83 mmol) and 9-amino-3-methyl-carbazole (0.20 g, 1 mmol) in 8 mL of dry tetrahydrofuran under an atmosphere of nitrogen. The resulting solution was stirred for 17 h at ambient temperature. After completion of the reaction, the reaction mixture was quenched with a saturated aqueous solution of sodium bicarbonate and extracted twice with dichloromethane. The organic phase was washed with brine, dried over anhydrous sodium sulfate and the solvent was removed under reduced pressure. The title compound as a beige solid (0.42 g, 59%) was obtained after recrystallization from dichloromethane/hexane.

$^1$H-NMR (400 MHz, DMSO-$d_6$) δ 9.14 (s, 1H), 8.23 (d, J=9.1 Hz, 2H), 8.09-8.15 (m, 4H), 7.96 (s, 1H), 7.70 (d, J=7.3 Hz, 1H), 7.64 (d, J=8.2 Hz, 1H), 7.48-7.55 (m, 2H), 7.22-7.30 (m, 2H), 7.10-7.18 (m, 5H), 6.29-6.34 (m, 2H), 6.13-6.21 (m, 2H), 5.90-5.95 (m, 2H), 4.08-4.14 (m, 8H), 2.43 (s, 3H), 1.76-1.79 (m, 4H), 1.59-1.68 (m, 4H), 1.40-1.49 (m, 8H); MALDI-TOF (CHCA) 887.35 (M$^+$+Na).

Example 3

Synthesis of Compound 3

Synthesis of 9-nitroso-3-fluorocarbazole

A solution of sodium nitrite (0.41 g, 6 mmol) in 2 mL of deionized water was added dropwise to a suspension of 3-fluorocarbazole (0.56 g, 3 mmol) and 50% aqueous solution of sulfuric acid (2 mL) in 15 mL of diethyl ether at 0° C. The reaction mixture was stirred for 1 h at 0° C. under nitrogen atmosphere. The reaction mixture was extracted with diethyl ether, dried over sodium sulfate and concentrated under reduced pressure to yield 0.66 g of the title compound as a solid which was used in the next step without further purification Synthesis of 9-amino-3-fluorocarbazole A solution of 9-nitroso-3-fluorocarbazole (0.66 g, 3 mmol) in anhydrous diethyl ether (10 mL) was added dropwise to a suspension of lithium aluminum hydride (0.23 g, 6 mmol) and 15 mL of anhydrous diethyl ether at 0° C. The grey suspension was stirred at room temperature for 18 h. The reaction mixture was quenched by addition of 10 mL of methanol at 0° C. and saturated Rochelle's salt solution, extracted with ethyl acetate, washed with brine and dried over sodium sulfate. The solvent was removed under reduced pressure and the residue was purified by flash column chromatography on silica gel using a 1:1 mixture of hexane/dichloromethane to give the title compound as a pale-yellow solid (0.19 g, 32% for 2 steps).

$^1$H-NMR (400 MHz, DMSO-$d_6$) δ 8.11 (d, J=7.8 Hz, 1H), 7.95 (dd, J=9.4, 2.5 Hz, 1H), 7.54-7.58 (m, 2H), 7.44-7.48 (m, 1H), 7.30 (td, J=9.3, 2.7 Hz, 1H), 7.13-7.17 (m, 1H), 5.85 (s, 2H).

Synthesis of Benzoic acid 4-[[(6-(acryloxy)hexyl)oxy]benzoyl]oxy]-2-[((1-E)-(3-fluoro-9H-carbazol)imino)methyl]-1,4-phenylene] ester (±) 10-Camphorsulfonic acid (18.6 mg, 0.08 mmol) was added to a solution of [3-formyl-4-[4-(6-prop-2-enoyloxyhexoxy)benzoyl]oxy-phenyl] 4-(6-prop-2-enoyloxyhexoxy)benzoate described in example 1 (0.51 g, 0.75 mmol) and 9-aminocarbazole (0.18 g, 0.9 mmol) in 8 mL of dry tetrahydrofuran under an atmosphere of nitrogen. The resulting solution was stirred for 4 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a beige solid (0.59 g, 90%) was obtained after recrystallization from dichloromethane/hexane.

$^1$H-NMR (400 MHz, DMSO-$d_6$) δ 9.14 (s, 1H), 8.20-8.26 (m, 4H), 8.15 (d, J=2.3 Hz, 1H), 7.97 (d, J=7.8 Hz, 1H), 7.73 (d, J=8.2 Hz, 1H), 7.66 (dt, J=8.7, 3.4 Hz, 2H), 7.32-7.41 (m, 3H), 7.00-7.08 (m, 6H), 6.41 (dt, J=17.4, 1.6 Hz, 2H), 6.10-6.17 (m, 2H), 5.83 (dq, J=10.5, 1.5 Hz, 2H), 4.20 (t, J=6.6 Hz, 4H), 4.08 (td, J=6.4, 3.2 Hz, 4H), 1.83-1.91 (m, 4H), 1.70-1.78 (m, 4H), 1.45-1.60 (m, 8H); MALDI-TOF (CHCA) 891.33 (M$^+$+Na).

Example 4

Synthesis of Compound 4

Synthesis of 9-nitroso-2-fluorocarbazole

A solution of sodium nitrite (0.41 g, 6 mmol) in 2 mL of deionized water was added dropwise to a suspension of 3-fluorocarbazole (0.56 g, 3 mmol) and 50% aqueous solution of sulfuric acid (2 mL) in 15 mL of diethyl ether at 0° C. The reaction mixture was stirred for 1 h at 0° C. under nitrogen atmosphere. The reaction mixture was extracted with diethyl ether, dried over sodium sulfate and concentrated under reduced pressure to yield 0.60 g of the title compound as a solid which was used in the next step without further purification Synthesis of 9-amino-2-fluorocarbazole A solution of 9-nitroso-2-fluorocarbazole (0.59 g, 3 mmol) in anhydrous diethyl ether (10 mL) was added dropwise to a suspension of lithium aluminum hydride (0.23 g, 6 mmol) and 15 mL of anhydrous diethyl ether at 0° C. The grey suspension was stirred at room temperature for 19 h. The reaction mixture was quenched by addition of 10 mL of methanol at 0° C. and saturated Rochelle's salt solution, extracted with ethyl acetate, washed with brine and dried over sodium sulfate. The solvent was removed under reduced pressure and the residue was purified by flash column chromatography on silica gel using a 1:1 mixture of hexane/dichloromethane to give the title compound as a pale-yellow solid (0.17 g, 26% for 2 steps).

$^1$H-NMR (400 MHz, DMSO-$d_6$) δ 8.08-8.13 (m, 2H), 7.56-7.58 (m, 1H), 7.41-7.45 (m, 1H), 7.30 (dd, J=10.1, 2.3 Hz, 1H), 7.16-7.20 (m, 1H), 6.96-7.01 (m, 1H), 5.86 (s, 2H).

Synthesis of Benzoic acid 4-[[(6-(acryloxy)hexyl)oxy]benzoyl]oxy]-2-[((1-E)-(2-fluoro-9H-carbazol)imino)methyl]-1,4-phenylene] ester (±) 10-Camphorsulfonic acid (16.3 mg, 0.07 mmol) was added to a solution of [3-formyl-4-[4-(6-prop-2-enoyloxyhexoxy)benzoyl]oxy-phenyl] 4-(6-prop-2-enoyloxyhexoxy)benzoate described in example 1 (0.48 g, 0.70 mmol) and 9-aminocarbazole (0.167 g, 0.83 mmol) in 7 mL of dry tetrahydrofuran under an atmosphere of nitrogen. The resulting solution was stirred for 2 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a beige solid (0.47 g, 77%) was obtained after recrystallization from dichloromethane/hexane.

$^1$H-NMR (400 MHz, DMSO-$d_6$) δ 9.20 (s, 1H), 8.13-8.24 (m, 7H), 7.74-7.76 (m, 1H), 7.51-7.57 (m, 3H), 7.25-7.30 (m, 2H), 7.09-7.16 (m, 5H), 6.29-6.34 (m, 2H), 6.13-6.21 (m, 2H), 5.91-5.95 (m, 2H), 4.07-4.13 (m, 8H), 1.74-1.80 (m, 4H), 1.61-1.68 (m, 4H), 1.40-1.51 (m, 8H); MALDI-TOF (CHCA) 891.34 (M$^+$+Na).

Example 5

Synthesis of Compound 5

Synthesis of 9-nitroso-3-tert-butylcarbazole

A solution of sodium nitrite (0.28 g, 4 mmol) in 1.2 mL of deionized water was added dropwise to a suspension of 3-tert-butylcarbazole (0.45 g, 2 mmol) and 50% aqueous solution of sulfuric acid (1.2 mL) in 10 mL of diethyl ether at 0° C. The reaction mixture was stirred for 30 min at 0° C. under nitrogen atmosphere. The reaction mixture was extracted with diethyl ether, dried over sodium sulfate and concentrated under reduced pressure to yield 0.49 g of the title compound as a solid which was used in the next step without further purification Synthesis of 9-amino-3-tert-butylcarbazole A solution of 9-nitroso-3-tert-butylcarbazol (0.49 g, 3 mmol) in anhydrous tetrahydrofuran (7 mL) was added dropwise to a suspension of lithium aluminum hydride (0.19 g, 6 mmol) and 10 mL of anhydrous tetrahydrofuran at 0° C. The suspension was stirred at room temperature for 1 h. The reaction mixture was quenched by addition of 10 mL of methanol at 0° C. and saturated Rochelle's salt solution, extracted with ethyl acetate, washed with brine and dried over sodium sulfate. The solvent was removed under reduced pressure and the residue was purified by flash column chromatography on silica gel using a 7:3 mixture of hexane/dichloromethane to give the title compound as a yellow solid (0.17 g, 35% for 2 steps).

$^1$H-NMR (400 MHz, DMSO-$d_6$) δ 8.08-8.11 (m, 2H), 7.47-7.55 (m, 3H), 7.40 (td, J=7.7, 1.1 Hz, 1H), 7.10-7.14 (m, 1H), 5.75 (s, 2H), 1.39 (s, 9H).

Synthesis of Benzoic acid 4-[[(6-(acryloxy)hexyl)oxy]benzoyl]oxy]-2-[((1-E)-(3-tert-butyl-9H-carbazol)imino)methyl]-1,4-phenylene] ester (±) 10-Camphorsulfonic acid (13 mg, 0.06 mmol) was added to a solution of [3-formyl-4-[4-(6-prop-2-enoyloxyhexoxy)benzoyl]oxy-phenyl] 4-(6-prop-2-enoyloxyhexoxy)benzoate described in example 1 (0.40 g, 0.58 mmol) and 9-amino-3-tert-butylcarbazole (0.168 g, 0.70 mmol) in 6 mL of dry tetrahydrofuran under an atmosphere of nitrogen. The resulting solution was stirred for 16 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a beige solid (0.46 g, 88%) was obtained after recrystallization from dichloromethane/hexane.

$^1$H-NMR (400 MHz, DMSO-$d_6$) δ 9.16 (s, 1H), 8.25 (d, J=8.7 Hz, 2H), 8.13-8.20 (m, 5H), 7.74 (d, J=8.2 Hz, 1H), 7.49-7.59 (m, 3H), 7.14-7.33 (m, 7H), 6.29-6.34 (m, 2H), 6.13-6.21 (m, 2H), 5.91-5.95 (m, 2H), 4.10-4.14 (m, 8H), 1.75-1.81 (m, 4H), 1.62-1.69 (m, 4H), 1.41-1.51 (m, 8H), 1.35 (s, 9H); MALDI-TOF (CHCA) 929.37 (M$^+$+Na).

Example 6

Synthesis of Compound 6

Synthesis of 9-amino-3,6-dimethylcarbazole

To a suspension of 3,6-dimethylcarbazole (1.88 g, 9.6 mmol) and potassium hydroxide (8.6 g, 154 mmol) in dry DMF (19 mL), solution of Hydroxylamine-O-sulfonic acid (HOSA) (2.17 g, 19.2 mmol) in dry DMF (38 mL) was added dropwise for 10 min at 0° C. The reaction mixture was stirred at room temperature and quenched with water and extracted with a 1:2 mixture of ethyl acetate/hexane. The organic phase was successively washed with water, brine, dried over anhydrous sodium sulfate and the solvent was removed under reduced pressure. The residue was purified by flash column chromatography on silica gel using a 1:4 mixture of ethyl acetate/hexane to give the title compound as a white solid (1.7 g, 85%).

$^1$H-NMR (400 MHz, DMSO-$d_6$) δ 7.82 (s, 2H), 7.42 (d, J=8.2 Hz, 2H), 7.23 (dd, J=8.2, 1.4 Hz, 2H), 5.70 (s, 2H), 2.45 (s, 6H).

Synthesis of Benzoic acid 4-[[(6-(acryloxy)hexyl)oxy]benzoyl]oxy]-2-[((1-E)-(3,6-dimethyl-9H-carbazol)imino)methyl]-1,4-phenylene] ester (±) 10-Camphorsulfonic acid (46.5 mg, 0.2 mmol) was added to a solution of [3-formyl-4-[4-(6-prop-2-enoyloxyhexoxy)benzoyl]oxy-phenyl] 4-(6-prop-2-enoyloxyhexoxy)benzoate described in example 1 (1.37 g, 2.0 mmol) and 9-amino-3,6-dimethylcarbazole (0.50 g, 2.4 mmol) in 20 mL of dry tetrahydrofuran under an atmosphere of nitrogen. The resulting solution was stirred for 16 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a beige solid (541 mg, 74%) was obtained after recrystallization from dichloromethane/hexane.

$^1$H-NMR (400 MHz, DMSO-$d_6$) δ 9.08 (s, 1H), 8.22 (d, J=9.1 Hz, 2H), 8.14 (d, J=8.7 Hz, 2H), 8.12 (d, J=2.7 Hz, 1H), 7.90 (s, 2H), 7.59 (d, J=8.2 Hz, 2H), 7.53 (d, J=8.7 Hz, 1H), 7.48 (dd, J=8.7, 2.7 Hz, 1H), 7.18 (d, J=8.7 Hz, 2H), 7.14 (d, J=8.7 Hz, 2H), 7.08 (dd, J=8.7, 1.4 Hz, 2H), 6.29-6.34 (m, 2H), 6.12-6.21 (m, 2H), 5.90-5.95 (m, 2H), 4.06-4.15 (m, 8H), 2.42 (s, 6H), 1.77 (td, J=12.8, 6.6 Hz, 4H), 1.59-1.68 (m, 4H), 1.41-1.52 (m, 8H); MALDI-TOF (CHCA) 901.35 (M$^+$+Na).

Example 7

Synthesis of Compound 7

Synthesis of 2-[(E)-carbazol-9-yliminomethyl]benzene-1,4-diol

To a solution of 9-aminocarbazole (0.33 g, 1.84 mmol) in dry ethanol (16.7 mL), 2,5-dihydroxybenzaldehyde (0.23 g, 1.67 mmol) was added. The reaction mixture was refluxed with stirring for 4 hours at ambient temperature. After completion of the reaction, the reaction mixture was cooled to 0° C. resulting in precipitation. Filtration and washing with hexane gave the title compound as a pale-yellow solid (0.42 g, 83%).

$^1$H-NMR (400 MHz, DMSO-$d_6$) δ 9.33 (s, 1H), 8.21 (d, J=7.8 Hz, 2H), 7.80 (d, J=8.2 Hz, 2H), 7.49-7.53 (m, 2H), 7.38 (d, J=2.7 Hz, 1H), 7.28-7.32 (m, 2H), 6.77-6.82 (m, 2H).

Synthesis of [2-[(E)-carbazol-9-yliminomethyl]-4-hydroxy-phenyl] 4-propylcyclohexanecarboxylate To a solution of 2-[(E)-carbazol-9-yliminomethyl]benzene-1,4-diol (0.5 g, 1.65 mmol), trans-4-propylcyclohexanecarboxylic acid (295 mg, 1.73 mmol) and 4-dimethylaminopyridine (DMAP) (20.8 mg, 0.17 mmol) in dry dichloromethane (2 mL), 1-(3-dimethylaminopropyl)-3-ethylcarbodiimide (EDC) (320 μL, 1.82 mmol) was added. The reaction mixture was stirred for 23 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The residue was purified by flash column chromatography on silica gel using a 1:8 mixture of ethyl acetate/hexane to give the title compound as a beige solid (452 mg, 60%).

$^1$H-NMR (400 MHz, DMSO-$d_6$) δ 9.40 (s, 1H), 8.24 (d, J=7.8 Hz, 2H), 7.88 (d, J=8.2 Hz, 2H), 7.70 (d, J=2.7 Hz, 1H), 7.52-7.56 (m, 2H), 7.34 (t, J=7.5 Hz, 2H), 7.07 (dd, J=8.7, 2.7 Hz, 1H), 6.99 (d, J=8.7 Hz, 1H), 2.07-2.11 (m, 2H), 1.78-1.82 (m, 2H), 1.41-1.51 (m, 2H), 1.14-1.34 (m, 6H), 0.93-1.03 (m, 2H), 0.86 (t, J=7.3 Hz, 3H).

Synthesis of [4-[trans-4-[[(propylcyclohexyl)carbonyl]oxy]]-2-[(1-E)-(9H-carbazol-9-amino)]-1,4-(N-phenylmethylene)] ester-4-(acryloxyhexyloxy)benzoic acid (Compound 7)

To a solution of [2-[(E)-carbazol-9-yliminomethyl]-4-hydroxy-phenyl] 4-propylcyclohexanecarboxylate (452 mg, 1 mmol), 4-[(6-(Acryloyloxy-hex-1-yloxy)benzoic acid (321 mg, 1.1 mmol) and 4-dimethylaminopyridine (DMAP) (12.2 mg, 0.1 mmol) in dry dichloromethane (2 mL), 1-(3-dimethylaminopropyl)-3-ethylcarbodiimide (EDC) (211 μL, 1.2 mmol) was added. The reaction mixture was stirred for 3 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a white solid (1.51 g, 86%) was obtained after recrystallization from dichloromethane/hexane.

$^1$H-NMR (400 MHz, DMSO-$d_6$) δ 9.18 (s, 1H), 8.16-8.23 (m, 4H), 7.97 (d, J=2.7 Hz, 1H), 7.73 (d, J=7.8 Hz, 2H), 7.50 (d, J=9.1 Hz, 1H), 7.26-7.37 (m, 5H), 7.14-7.17 (m, 2H), 6.29-6.33 (m, 1H), 6.13-6.20 (m, 1H), 5.92 (dd, J=10.1, 1.8 Hz, 1H), 4.11 (t, J=6.6 Hz, 4H), 2.14 (dd, J=13.7, 3.2 Hz, 2H), 1.73-1.84 (m, 4H), 1.61-1.68 (m, 2H), 1.40-1.56 (m, 6H), 1.16-1.35 (m, 4H), 0.96-1.08 (m, 2H), 0.87 (t, J=7.3 Hz, 3H); MALDI-TOF (CHCA) 751.35 (M$^+$+Na).

Example 8

Synthesis of Compound 8

Synthesis of 1-methyl-2-(2-nitrophenyl)benzene

A round-bottom flask was charged with 2-methylphenylboronic acid (2.04 g, 15 mmol), 2-chloronitrobenzene (1.58 g, 10 mmol), tripotassium phosphate (6.37 g, 30 mmol), palladium (II) acetate (67 mg, 0.3 mmol), dicyclohexyl-[2-(2,4,6-triisopropylphenyl)phenyl]phosphane (X-Phos) (286 mg, 0.6 mmol), tetrahydrofuran (20 mL), and water (2 mL). The mixture was stirred at 40° C. under an atmosphere of nitrogen for 2 h. The reaction mixture was cooled to ambient temperature, diluted with dichloromethane, filtered through celite pad. The filtrate was washed with water and brine. The organic layer was dried over anhydrous sodium sulfate and the solvent was removed under reduced pressure. The residue was purified by flash column chromatography on silica gel using ethyl acetate/hexane to give the title compound as a yellow oil (1.94 g, 91%).

$^1$H-NMR (400 MHz, DMSO-$d_6$) δ 8.05 (dd, J=8.0, 1.1 Hz, 1H), 7.77 (td, J=7.4, 1.2 Hz, 1H), 7.65 (td, J=7.8, 1.4 Hz, 1H), 7.43 (dd, J=7.3, 1.4 Hz, 1H), 7.28-7.33 (m, 2H), 7.20-7.26 (m, 1H), 7.08 (d, J=7.3 Hz, 1H), 2.03 (s, 3H).

Synthesis of 4-methyl-9H-carbazole

A round-bottom flask was charged with 2-nitro-2'-methylbiphenyl (1.94 g, 9.1 mmol), triphenylphosphine (5.97 g, 22.7 mmol), and o-dichlorobenzene (18 mL). The mixture was stirred at 175° C. for 17 h. The reaction mixture was cooled to ambient temperature and purified by flash column chromatography on silica gel using dichloromethane/hexane to give the title compound as a beige solid (1.23 g, 75%).

$^1$H-NMR (400 MHz, DMSO-$d_6$) δ 11.27 (s, 1H), 8.10 (d, J=7.8 Hz, 1H), 7.48 (d, J=7.8 Hz, 1H), 7.37 (td, J=7.5, 0.9 Hz, 1H), 7.31 (d, J=7.8 Hz, 1H), 7.26 (t, J=7.5 Hz, 1H), 7.14-7.18 (m, 1H), 6.93 (d, J=6.9 Hz, 1H), 2.79 (s, 3H).

Synthesis of 4-methylcarbazol-9-amine

To a suspension of 4-methylcarbazole (1.23 g, 6.79 mmol) and potassium hydroxide (3.05 g, 54.3 mmol) in dry dimethylformamide (DMF) (14 mL), solution of hydroxylamine-O-sulfonic acid (HOSA) (1.54 g, 13.6 mmol) in dry DMF (28 mL) was added dropwise for 30 min at 0° C. The reaction mixture was quenched with water and extracted with ethyl acetate. The organic phase was successively washed with water three times, brine, dried over anhydrous sodium sulfate. The solvent was removed under reduced pressure to give the title compound as a beige solid (1.27 g, 95%).

$^1$H-NMR (400 MHz, DMSO-$d_6$) δ 8.10 (d, J=7.8 Hz, 1H), 7.61 (d, J=8.2 Hz, 1H), 7.42-7.49 (m, 2H), 7.32-7.37 (m, 1H), 7.14-7.19 (m, 1H), 6.95 (d, J=7.3 Hz, 1H), 5.81 (s, 2H), 2.79 (s, 3H).

Synthesis of Benzoic acid [3-[(E)-(4-methylcarbazol-9-yl)iminomethyl]-4-[4-(6-prop-2-enoyloxy-hexoxy)benzoyl]oxy-phenyl] 4-(6-prop-2-enoyloxyhexoxy)benzoate (±) 10-Camphorsulfonic acid (34.8 mg, 0.15 mmol) was added to a solution of [3-formyl-4-[4-(6-prop-2-enoyloxy-hexoxy)benzoyl]oxy-phenyl] 4-(6-prop-2-enoyloxyhexoxy) benzoate described in example 1 (1.03 g, 1.5 mmol) and 9-amino-4-methylcarbazole (0.31 g, 1.58 mmol) in 15 mL of dry tetrahydrofuran under an atmosphere of nitrogen. The resulting solution was stirred for 22 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a beige solid (1.03 g, 79%) was obtained after recrystallization from dichloromethane/hexane.

$^1$H-NMR (400 MHz, DMSO-$d_6$) δ 9.21 (s, 1H), 8.22 (d, J=8.7 Hz, 2H), 8.12-8.16 (m, 4H), 7.77-7.79 (m, 1H), 7.61 (d, J=8.2 Hz, 1H), 7.51-7.57 (m, 2H), 7.27-7.34 (m, 2H), 7.14-7.23 (m, 5H), 7.07 (d, J=7.3 Hz, 1H), 6.29-6.34 (m, 2H), 6.13-6.21 (m, 2H), 5.90-5.95 (m, 2H), 4.10-4.13 (m, 8H), 2.78 (s, 3H), 1.74-1.80 (m, 4H), 1.60-1.68 (m, 4H), 1.36-1.51 (m, 8H); MALDI-TOF (CHCA) 887.34 (M$^+$+Na).

Example 9

Synthesis of Compound 9

Synthesis of 4-fluoro-1-(4-fluorophenyl)-2-nitro-benzene

A round-bottom flask was charged with 4-fluorophenyl-boronic acid (2.10 g, 15 mmol), 1-chloro-4-fluoro-2-nitrobenzene (1.75 g, 10 mmol), tripotassium phosphate (6.37 g, 30 mmol), palladium (II) acetate (112 mg, 0.5 mmol), dicyclohexyl-[2-(2,4,6-triisopropylphenyl)phenyl]phosphane (X-Phos) (477 mg, 1 mmol), tetrahydrofuran (20 mL), and water (2 mL). The mixture was stirred at 40° C. under an atmosphere of nitrogen for 14 h. The reaction mixture was cooled to ambient temperature, diluted with dichloromethane, filtered through celite pad. The filtrate was washed with water and brine. The organic layer was dried over anhydrous sodium sulfate and the solvent was removed under reduced pressure. The residue was purified by flash column chromatography on silica gel using dichloromethane/hexane to give the title compound as a yellow solid (2.17 g, 92%).

$^1$H-NMR (400 MHz, CDCl$_3$) δ 7.60-7.63 (m, 1H), 7.33-7.43 (m, 2H), 7.23-7.28 (m, 2H), 7.09-7.15 (m, 2H).

Synthesis of 2,7-difluoro-9H-carbazole

A round-bottom flask was charged with 4-fluoro-2-nitro-4'-fluorobiphenyl (1.15 g, 4.89 mmol), triphenylphosphine (3.21 g, 12.2 mmol), and o-dichlorobenzene (10 mL). The mixture was stirred at 175° C. for 17 h. The reaction mixture was cooled to ambient temperature and purified by flash column chromatography on silica gel using dichloromethane/hexane to give the title compound as a beige solid (0.73 g, 74%).

$^1$H-NMR (400 MHz, DMSO-$d_6$) δ 11.48 (s, 1H), 8.09 (dd, J=8.7, 5.5 Hz, 2H), 7.25 (dd, J=10.1, 2.3 Hz, 2H), 6.97-7.02 (m, 2H).

Synthesis of 2,7-difluorocarbazol-9-amine

To a suspension of 2,7-difluorocarbazole (1.0 g, 5 mmol) and potassium hydroxide (2.24 g, 40 mmol) in dry DMF (10 mL), solution of hydroxylamine-O-sulfonic acid (HOSA) (1.13 g, 10 mmol) in dry DMF (20 mL) was added dropwise for 30 min at 0° C. The reaction mixture was quenched with water and extracted with ethyl acetate. The organic phase was successively washed with water three times, brine, dried over anhydrous sodium sulfate and the solvent was removed under reduced pressure. The residue was purified by flash column chromatography on silica gel using a ethyl acetate/hexane to give the title compound as a yellow solid (0.39 g, 36%).

$^1$H-NMR (400 MHz, DMSO-$d_6$) δ 8.10 (dd, J=8.7, 5.5 Hz, 2H), 7.30 (dd, J=10.1, 2.3 Hz, 2H), 6.98-7.03 (m, 2H), 5.90 (s, 2H).

Synthesis of [3-[(E)-(2,7-difluorocarbazol-9-yl)iminomethyl]-4-[4-(6-prop-2-enoyloxyhexoxy)benzoyl]oxy-phenyl] 4-(6-prop-2-enoyloxyhexoxy)benzoate (±) 10-Camphorsulfonic acid (39.7 mg, 0.17 mmol) was added to a solution of [3-formyl-4-[4-(6-prop-2-enoyloxy-hexoxy)benzoyl]oxy-phenyl] 4-(6-prop-2-enoyloxyhexoxy) benzoate described in example 1 (1.17 g, 1.71 mmol), 9-amino-2,7-difluorocarbazole (0.39 g, 1.79 mmol), and 4-hydroxy-2,2,6,6-tetramethylpiperidine 1-oxyl free radical (0.3 mg, 0.002 mmol) in 17 mL of dry tetrahydrofuran under an atmosphere of nitrogen. The resulting solution was stirred under an atmosphere of nitrogen for 23 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a beige solid (1.38 g, 91%) was obtained after recrystallization from dichloromethane/hexane.

$^1$H-NMR (400 MHz, DMSO-$d_6$) δ 9.18 (s, 1H), 8.13-8.22 (m, 7H), 7.54-7.57 (m, 4H), 7.10-7.17 (m, 6H), 6.29-6.34 (m, 2H), 6.13-6.21 (m, 2H), 5.90-5.95 (m, 2H), 4.08-4.13 (m, 8H), 1.73-1.82 (m, 4H), 1.61-1.68 (m, 4H), 1.36-1.51 (m, 8H); MALDI-TOF (CHCA) 909.32 (M$^+$+Na).

Example 10

Synthesis of Compound 10

Synthesis of 3-methoxy-9H-carbazole

A round-bottom flask was charged with cyclohexanone (1.03 mL, 10 mmol), 4-methoxyphenylhydrazine hydrochloride (2.62 g, 15 mmol), and dry 1-methyl-2-pyrrolidone (NMP) (20 mL). The mixture was stirred at 140° C. for 19 h. The reaction mixture was cooled to ambient temperature, and quenched with water. The reaction mixture was quenched with water and extracted with ethyl acetate. The organic phase was washed with water twice and brine, dried over anhydrous sodium sulfate and the solvent was removed under reduced pressure. The residue was purified by flash column chromatography on silica gel using a ethyl acetate/hexane to give the title compound as an orange solid (0.61 g, 31%).

$^1$H-NMR (400 MHz, DMSO-d6) δ 11.01 (s, 1H), 8.07 (d, J=7.8 Hz, 1H), 7.66 (d, J=2.3 Hz, 1H), 7.31-7.43 (m, 3H), 7.07-7.11 (m, 1H), 7.00 (dd, J=8.7, 2.3 Hz, 1H), 3.83 (s, 3H)

Synthesis of 3-methoxycarbazol-9-amine

To a suspension of 3-methoxycarbazole (0.59 g, 3 mmol) and potassium hydroxide (1.35 g, 24 mmol) in dry DMF (6 mL), solution of hydroxylamine-O-sulfonic acid (HOSA) (0.68 g, 6 mmol) in dry DMF (12 mL) was added dropwise for 12 min at 0° C. The reaction mixture was quenched with water and extracted with ethyl acetate. The organic phase was successively washed with water three times, brine, dried over anhydrous sodium sulfate and the solvent was removed under reduced pressure. The residue was purified by flash column chromatography on silica gel using dichloromethane/hexane to give the title compound as a white solid (0.35 g, 55%).

$^1$H-NMR (400 MHz, DMSO-$d_6$) δ 8.07 (d, J=7.8 Hz, 1H), 7.67 (d, J=2.3 Hz, 1H), 7.53 (d, J=8.2 Hz, 1H), 7.48 (d, J=9.1 Hz, 1H), 7.38-7.42 (m, 1H), 7.07-7.12 (m, 2H), 5.75 (s, 2H), 3.84 (s, 3H)

Synthesis of [3-[(E)-(3-methoxycarbazol-9-yl)iminomethyl]-4-[4-(6-prop-2-enoyloxyhexoxy)benzoyl]oxy-phenyl] 4-(6-prop-2-enoyloxyhexoxy)benzoate (±) 10-Camphorsulfonic acid (35 mg, 0.15 mmol) was added to a solution of [3-formyl-4-[4-(6-prop-2-enoyloxyhexoxy)benzoyl]oxy-phenyl] 4-(6-prop-2-enoyloxyhexoxy)benzoate described in example 1 (1.03 g, 1.5 mmol), 9-amino-3-methoxycarbazole (0.33 g, 1.58 mmol), and 4-hydroxy-2,2,6,6-tetramethylpiperidine 1-oxyl free radical (TEMPO-OH) (3 mg, 0.02 mmol) in 15 mL of dry tetrahydrofuran under an atmosphere of nitrogen. The resulting solution was stirred for 19 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a beige solid (1.27 g, 96%) was obtained after recrystallization from dichloromethane/methanol.

$^1$H-NMR (400 MHz, DMSO-$d_6$) δ 9.12 (s, 1H), 8.23 (d, J=8.7 Hz, 2H), 8.12-8.16 (m, 4H), 7.76 (d, J=2.3 Hz, 1H), 7.65-7.71 (m, 2H), 7.47-7.55 (m, 2H), 7.22-7.31 (m, 2H), 7.14-7.19 (m, 4H), 6.87 (dd, J=8.9, 2.5 Hz, 1H), 6.29-6.34 (m, 2H), 6.13-6.21 (m, 2H), 5.90-5.95 (m, 2H), 4.08-4.15 (m, 8H), 1.74-1.82 (m, 4H), 1.59-1.69 (m, 4H), 1.37-1.51 (m, 8H); MALDI-TOF (CHCA) 903.34 (M$^+$+Na).

Example 11

Synthesis of Compound 11

Synthesis of 3-(4-tert-butylphenyl)-9H-carbazole

A round-bottom flask was charged with 3-iodocarbazole (1.47 g, 5 mmol), 4-tert-butylphenylboronic acid (1.34 g, 7.5 mmol), tripotassium phosphate (3.18 g, 15 mmol), palladium (II) acetate (56.1 mg, 0.25 mmol), dicyclohexyl-[2-(2,4,6-triisopropylphenyl)-phenyl]phosphane (X-Phos) (238 mg, 0.5 mmol), tetrahydrofuran (10 mL), and water (1 mL). The mixture was stirred at 40° C. under an atmosphere of nitrogen for 23 h. The reaction mixture was cooled to ambient temperature, diluted with dichloromethane, filtered through celite pad. The solvent was removed under reduced pressure. The residue was purified by flash column chromatography on silica gel using ethyl acetate/hexane to give the title compound as a beige solid (1.29 g, 86%).

$^1$H-NMR (400 MHz, DMSO-$d_6$) δ 11.28 (s, 1H), 8.38 (d, J=1.8 Hz, 1H), 8.18 (d, J=7.8 Hz, 1H), 7.66-7.69 (m, 3H), 7.53 (d, J=8.2 Hz, 1H), 7.46-7.50 (m, 3H), 7.36-7.40 (m, 1H), 7.14-7.18 (m, 1H), 1.33 (s, 9H)

Synthesis of 3-(4-tert-butylphenyl)carbazol-9-amine

To a suspension of 3-(4-tert-butylphenyl)carbazole (0.57 g, 1.9 mmol) and potassium tert-butoxide (0.32 g, 2.8 mmol) in dry 1-methyl-2-pyrrolidone (NMP) (26 mL), solution of O-(4-nitrobenzoyl)hydroxylamine (NBzONH$_2$) (0.42 g, 2.3 mmol) in dry 1-methyl-2-pyrrolidone (NMP) (15 mL) was added dropwise for 10 min at ambient temperature. The reaction mixture was stirred at room temperature for 10 min and quenched with water and extracted with ethyl acetate. The organic phase was successively washed with water three times, brine, dried over anhydrous sodium sulfate. The solvent was removed under reduced pressure to give the title compound as a beige solid (0.56 g, 94%).

$^1$H-NMR (400 MHz, DMSO-$d_6$) δ 8.39 (d, J=1.4 Hz, 1H), 8.18 (d, J=7.8 Hz, 1H), 7.75 (dd, J=8.7, 1.8 Hz, 1H), 7.66-7.70 (m, 2H), 7.64 (d, J=8.7 Hz, 1H), 7.59 (d, J=8.2 Hz, 1H), 7.44-7.50 (m, 3H), 7.14-7.20 (m, 1H), 5.86 (s, 2H), 1.33 (s, 9H)

Synthesis of [3-[(E)-[3-(4-tert-butylphenyl)carbazol-9-yl]iminomethyl]-4-[4-(6-prop-2-enoyloxyhexoxy)benzoyl]oxy-phenyl] 4-(6-prop-2-enoyloxyhexoxy)benzoate (±) 10-Camphorsulfonic acid (39 mg, 0.17 mmol) was added to a solution of [3-formyl-4-[4-(6-prop-2-enoyloxyhexoxy)benzoyl]oxy-phenyl] 4-(6-prop-2-enoyloxyhexoxy)benzoate described in example 1 (1.17 g, 1.7 mmol), 9-amino-3-(4-tert-butylphenyl)carbazole (0.56 g, 1.78 mmol), and 4-hydroxy-2,2,6,6-tetramethylpiperidine 1-oxyl free radical (TEMPO-OH) (3 mg, 0.02 mmol) in dry tetrahydrofuran (17 mL) under an atmosphere of nitrogen. The resulting solution was stirred for 17 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a gray solid (1.40 g, 84%) was obtained after recrystallization from dichloromethane/methanol.

$^1$H-NMR (400 MHz, DMSO-$d_6$) δ 9.22 (s, 1H), 8.46 (d, J=1.8 Hz, 1H), 8.24-8.26 (m, 3H), 8.13-8.17 (m, 3H), 7.73-7.78 (m, 2H), 7.66 (d, J=8.7 Hz, 2H), 7.48-7.57 (m, 5H), 7.27-7.36 (m, 2H), 7.14-7.20 (m, 4H), 6.28-6.34 (m, 2H), 6.11-6.21 (m, 2H), 5.89-5.95 (m, 2H), 4.06-4.14 (m, 8H), 1.73-1.80 (m, 4H), 1.58-1.69 (m, 4H), 1.36-1.51 (m, 8H), 1.32 (s, 9H).

Example 12

Synthesis of Compound 12

Synthesis of 3-(o-tolyl)-9H-carbazole

A round-bottom flask was charged with 3-iodocarbazole (1.47 g, 5 mmol), 2-methylphenylboronic acid (1.02 g, 7.5 mmol), tripotassium phosphate (3.18 g, 15 mmol), palladium (II) acetate (56.1 mg, 0.25 mmol), dicyclohexyl-[2-(2,4,6-triisopropylphenyl)-phenyl]phosphane (X-Phos) (238 mg, 0.5 mmol), tetrahydrofuran (10 mL), and water (1 mL).

The mixture was stirred at 40° C. under an atmosphere of nitrogen for 19 h. The reaction mixture was cooled to ambient temperature, diluted with dichloromethane, filtered through celite pad. The solvent was removed under reduced pressure. The residue was purified by flash column chromatography on silica gel using ethyl acetate/hexane to give the title compound as an orange solid (0.91 g, 71%).

$^1$H-NMR (400 MHz, DMSO-$d_6$) δ 11.29 (s, 1H), 8.14 (d, J=7.8 Hz, 1H), 8.06 (s, 1H), 7.48-7.52 (m, 2H), 7.36-7.40 (m, 1H), 7.23-7.35 (m, 5H), 7.12-7.16 (m, 1H), 2.28 (s, 3H)

Synthesis of 3-(o-tolyl)carbazol-9-amine

To a suspension of 3-(2-methylphenyl)carbazole (0.91 g, 3.5 mmol) and potassium tert-butoxide (0.59 g, 5.25 mmol) in dry 1-methyl-2-pyrrolidone (NMP) (45.5 mL), solution of O-(4-nitrobenzoyl)hydroxylamine (NBzONH$_2$) (0.77 g, 4.2 mmol) in dry 1-methyl-2-pyrrolidone (NMP) (28 mL) was added dropwise for 25 min at ambient temperature. The reaction mixture was stirred at room temperature for 30 min and quenched with water and extracted with ethyl acetate. The organic phase was successively washed with water three times, brine, dried over anhydrous sodium sulfate. The solvent was removed under reduced pressure to give the title compound as a brown oil (0.85 g, quant.).

$^1$H-NMR (400 MHz, DMSO-$d_6$) δ 8.14 (d, J=7.8 Hz, 1H), 8.06 (d, J=0.9 Hz, 1H), 7.61 (t, J=8.0 Hz, 2H), 7.40-7.47 (m, 2H), 7.24-7.33 (m, 4H), 7.14-7.18 (m, 1H), 5.86 (s, 2H), 2.28 (s, 3H)

Synthesis of [3-[(E)-[3-(o-tolyl)carbazol-9-yl]iminomethyl]-4-[4-(6-prop-2-enoyloxyhexoxy)benzoyl]oxy-phenyl] 4-(6-prop-2-enoyloxyhexoxy)benzoate (±) 10-Camphorsulfonic acid (32.5 mg, 0.14 mmol) was added to a solution of [3-formyl-4-[4-(6-prop-2-enoyloxyhexoxy)benzoyl]oxy-phenyl] 4-(6-prop-2-enoyloxyhexoxy)benzoate described in example 1 (0.96 g, 1.4 mmol), 9-amino-3-(2-methylphenyl)carbazole (0.41 g, 1.51 mmol), 4-hydroxy-2,2,6,6-tetramethylpiperidine 1-oxyl free radical (TEMPO-OH) (2.4 mg, 0.014 mmol) in 14 mL of dry tetrahydrofuran under an atmosphere of nitrogen. The resulting solution was stirred for 22 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a beige solid (1.03 g, 78%) was obtained after recrystallization from dichloromethane/methanol.

$^1$H-NMR (400 MHz, DMSO-$d_6$) δ 9.24 (s, 1H), 8.25 (d, J=9.1 Hz, 2H), 8.22 (d, J=7.8 Hz, 1H), 8.14-8.18 (m, 4H), 7.78 (d, J=8.2 Hz, 1H), 7.73 (d, J=8.7 Hz, 1H), 7.51-7.57 (m, 2H), 7.26-7.36 (m, 6H), 7.19-7.22 (m, 1H), 7.14-7.17 (m, 4H), 6.29-6.34 (m, 2H), 6.12-6.20 (m, 1H), 5.90-5.94 (m, 2H), 4.05-4.14 (m, 8H), 2.24 (s, 3H), 1.68-1.80 (m, 4H), 1.57-1.67 (m, 4H), 1.35-1.51 (m, 8H).

Example 13

Synthesis of Compound 13

Synthesis of 4-chlorocarbonyloxybutyl prop-2-enoate

To a solution of triphosgene (12.5 g, 42 mmol) in dry dichloromethane (45 mL), the solution of 4-hydroxybutyl acrylate (16.6 mL, 120 mmol) in dry dichloromethane (30 mL) was added dropwise for 5 min at ambient temperature under an atmosphere of nitrogen. The mixture was cooled to −5° C. and the mixture of 4-hydroxy-2,2,6,6-tetramethylpiperidine 1-oxyl free radical (2 mg, 0.01 mmol), pyridine (9.69 mL, 120 mmol), and dry dichloromethane (48 mL) was added dropwise for 30 min. The reaction mixture was stirred for 22 h at ambient temperature. Dichloromethane was removed under reduced pressure, and the residue was filtered and washed with ethyl acetate twice. The solvent was removed under reduced pressure to give the title compound as a colourless oil (28.9 g, quant.).

$^1$H-NMR (400 MHz, CDCl$_3$) δ 6.41 (dd, J=17.2, 1.6 Hz, 1H), 6.12 (dd, J=17.4, 10.5 Hz, 1H), 5.85 (dd, J=10.5, 1.4 Hz, 1H), 4.37 (t, J=6.2 Hz, 2H), 4.21 (t, J=6.2 Hz, 2H), 1.76-1.89 (m, 4H)

Synthesis of 4-(4-prop-2-enoyloxybutoxycarbonyloxy)benzoic acid

To a solution of 4-hydroxybenzoic acid (9.54 g, 69.1 mmol) in dimethylformamide (DMF) (61 mL), and water (77 mL), 10% sodium hydroxide aqueous solution was added to adjust pH to 10. To the mixture, 4-chlorocarbonyloxybutyl prop-2-enoate (15.7 g, 76 mmol) was added slowly for 10 min. pH was adjusted to 10 by adding 10% sodium hydroxide aqueous solution. The reaction mixture was stirred for 22 h at ambient temperature and quenched with 1 M HCl aq. (pH 2) on ice bath. White precipitate was filtered and washed with water twice, and dried in vacuo to give the title compound as a white solid (22.8 g, quant.).

$^1$H-NMR (400 MHz, DMSO-$d_6$) δ 7.98 (d, J=8.7 Hz, 2H), 7.36 (d, J=8.7 Hz, 2H), 6.32 (dd, J=17.4, 1.4 Hz, 1H), 6.17 (dd, J=17.4, 10.5 Hz, 1H), 5.94 (dd, J=10.3, 1.6 Hz, 1H), 4.25 (t, J=5.9 Hz, 2H), 4.15 (t, J=5.9 Hz, 2H), 1.68-1.79 (m, 4H)

Synthesis of [3-formyl-4-[4-(4-prop-2-enoyloxybutoxycarbonyloxy)benzoyl]oxy-phenyl] 4-(4-prop-2-enoyloxybutoxycarbonyloxy)benzoate To a solution of 4-(4-prop-2-enoyloxybutoxycarbonyloxy)benzoic acid (6.78 g, 22 mmol) and 4-methoxyphenol (2,5 mg, 0.02 mmol) in anhydrous toluene (44 mL) and anhydrous dimethylformamide (DMF) (2 mL), oxalyl chloride (2.3 mL, 26 mmol) was added dropwise for 5 min at 45° C. After stirring for 18 h, the reaction mixture was cooled down to ambient temperature and added dropwise for 30 min at 0-5° C. to a solution of 2,5-dihydroxybenzaldehyde (1.38 g, 10 mmol) and N,N-dimethylcyclohexylamine (7.48 g, 50 mmol) in anhydrous DMA (33 mL). The reaction mixture was stirred at ambient temperature for 3 h. The reaction mixture was quenched by addition of 1 M HCl aq. and water on ice bath, extracted with dichloromethane and successively washed with water, brine, dried over sodium sulfate and concentrated under vacuo. The title compound was obtained as a white solid (3.26 g, 45%) after recrystallization from dichloromethane/methanol.

$^1$H-NMR (400 MHz, CDCl$_3$) δ 10.19 (s, 1H), 8.28-8.30 (m, 2H), 8.24-8.27 (m, 2H), 7.81 (d, J=2.7 Hz, 1H), 7.56 (dd, J=8.9, 3.0 Hz, 1H), 7.36-7.42 (m, 5H), 6.43 (dd, J=17.4, 1.4 Hz, 2H), 6.14 (dd, J=17.4, 10.5 Hz, 2H), 5.85 (dd, J=10.3, 1.6 Hz, 2H), 4.33-4.36 (m, 4H), 4.21-4.26 (m, 4H), 1.80-1.92 (m, 8H)

Synthesis of [3-[(E)-(3-methylcarbazol-9-yl)imi-nomethyl]-4-[4-(4-prop-2-enoyloxybutoxycarbony-loxy)benzoyl]oxy-phenyl] 4-(4-prop-2-enoyloxybu-toxycarbonyloxy)benzoate (±) 10-Camphorsulfonic acid (34.8 mg, 0.15 mmol) was added to a solution of [3-formyl-4-[4-(4-prop-2-enoyloxy-butoxycarbonyloxy)benzoyl]oxy-phenyl]4-(4-prop-2-enoy-loxybutoxycarbonyloxy)benzoate (1.08 g, 1.5 mmol) and 9-amino-3-methylcarbazole (0.31 g, 1.6 mmol) in 15 mL of dry tetrahydrofuran under an atmosphere of nitrogen. The resulting solution was stirred for 23 h at ambient temperature. After completion of the reaction, the reaction mixture was quenched with a saturated aqueous solution of sodium bicarbonate and extracted with dichloromethane. The organic phase was washed with brine, dried over anhydrous sodium sulfate and the solvent was removed under reduced pressure. The title compound as a beige solid (1.21 g, 89%) was obtained after recrystallization from dichloromethane/hexane.

$^1$H-NMR (400 MHz, DMSO-$d_6$) δ 9.21 (s, 1H), 8.38 (dd, J=6.6, 2.1 Hz, 2H), 8.28 (dd, J=6.9, 2.3 Hz, 2H), 8.21 (d, J=2.7 Hz, 1H), 8.11 (d, J=7.3 Hz, 1H), 7.97 (s, 1H), 7.72 (d, J=8.2 Hz, 1H), 7.62-7.66 (m, 1H), 7.52-7.60 (m, 6H), 7.23-7.32 (m, 2H), 7.12-7.15 (m, 1H), 6.31-6.37 (m, 2H), 6.15-6.22 (m, 2H), 5.93-5.97 (m, 2H), 4.27-4.32 (m, 4H), 4.16-4.18 (m, 4H), 2.44 (s, 3H), 1.71-1.81 (m, 8H).

Example 14

The phase transition temperatures and mesophase textures were determined by differential scanning calorimetry and polarized optical microscopy as described below using compounds 1-13 described in Examples 1 to 13 with compound R1 (Patent WO12141245) and compound R2 (Patent WO9700600) used as a comparative examples.

For the Polarized Optical Microscopy Measurements, 3 mg of compound was placed between two glass slides in a hot stage oven and heated from 25° C. to 200° C. then cooled down again to 25° C. Characteristic birefringent textures were analyzed using a polarized optical microscope.

For the Differential Scanning calorimetry Measurements, approximately 5 mg of compound was placed in a sealed aluminum pan was subjected to two successive heating-cooling circles at a scanning rate of 10° C./min. The transition temperatures were determined from the resulting endo/exothermic peaks of the DSC thermograms.

All phase transition temperature (T) resulting from the Polarized Optical Microscopy Measurements and from Differential Scanning calorimetry Measurements are summarized in Table 1. Compound states are indicated as "Cr" for solid crystal phase, "N" for nematic and "Iso" for the isotropic liquid state. Compounds 3 and 4 underwent thermal polymerization before reaching isotropization.

TABLE 1

| Compound | Heating stage (° C.) | | Cooling Stage (°) | |
|---|---|---|---|---|
| | Tcr-N | TN-iso | TN-iso | Tcr-N |
| R1 | 102 | 165 | 50 | 140 |
| R2 | 60 | 128 | 122 | <30 |
| 1 | 114 | 133 | 132 | 90 |
| 2 | 100 | 139 | 137 | 15 |
| 3 | 129 | >200 | >200 | 73 |
| 4 | 131 | >200 | >200 | 83 |
| 5 | 100 | 102 | 93 | 58 |
| 6 | 96 | 134 | 132 | 40 |
| 7 | 134 | 152 | 151 | 89 |
| 8 | 111 | 123 | 115 | 80 |
| 9 | 111 | 164 | 162 | 35 |
| 10 | 78 | 129 | 126 | <20 |
| 11 | 108 | 125 | 108 | 60 |
| 12 | <25 | 85 | 82 | <20 |
| 13 | 143 | 163 | 152 | 140 |

Compound R1

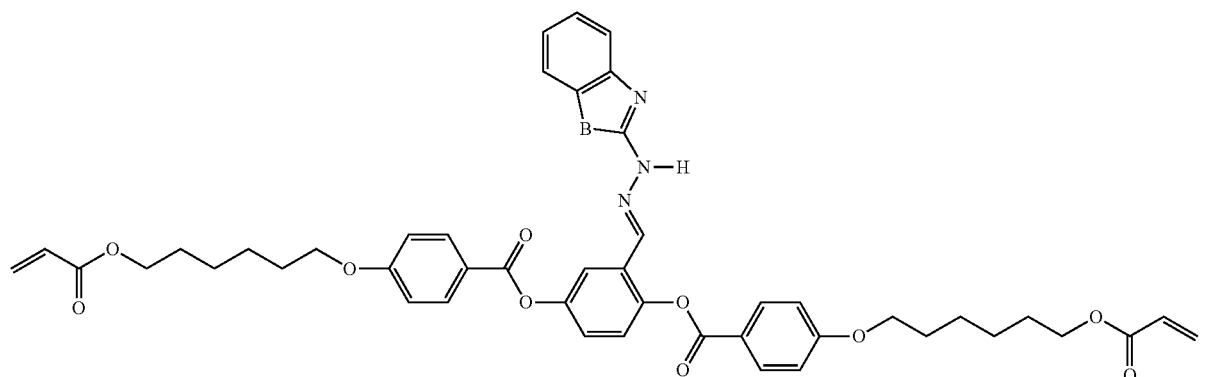

Compound R2

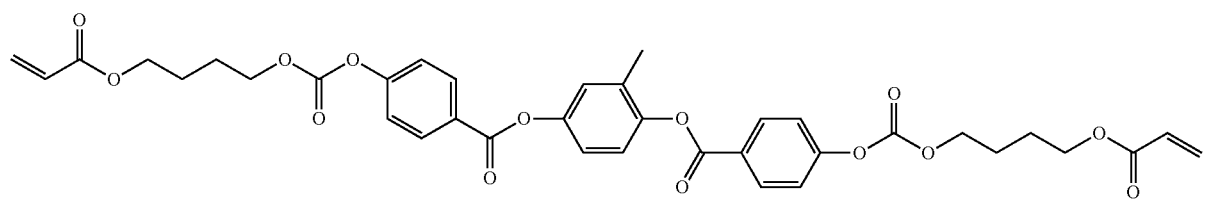

Examples 15

General Procedure for LC-Coated Film Preparation on Rubbed Substrate from the Compound 1 to 13

0.26 g of liquid crystal compound was dissolved in 830 μL of cyclopentanone. 13 μL of a 1 wt. % of cyclopentanone solution of BYK361 was added and the resulting solution was filtered through a 0.45 μm PTFE filter. 13 mg of Irgacure 907 was added to yield a polymerizable composition.

Polymerizable composition was applied to a glass substrate coated by a rubbed layer (manufactured by EHC). After drying/annealing the film for 4 minutes at the temperature shown in Table 2, the film was photocured using a UV spot cure (SP-7 manufactured by Ushio) at a dose of 1000 mJ/cm$^2$. UV exposure was performed at temperatures described in Table 2.

TABLE 2

| Compounds | Alignment temperature (° C.) | Curing Temperature (° C.) |
|---|---|---|
| 1 | 125 | 125 |
| 2 | 120 | 25 |
| 3 | 140 | 140 |
| 4 | 150 | 150 |
| 5 | 101 | 80 |
| 6 | 120 | 25 |
| 7 | 140 | 140 |
| 8 | 110 | 110 |
| 9 | 125 | 25 |
| 10 | 110 | 25 |
| 12 | 70 | 25 |
| 13 | 150 | 150 |

Example 16

The retardations in the visible region (400-700 nm) was measured by polarization rotation method using a polarized optical microscope, Senarmont compensator and optical filters. In plane retardation $R_0$ is determined using the following equation from the extinction position θ at a certain wavelength λ.

$$R_0 = \frac{\theta}{180}\lambda$$

Film thickness d is measured using a Dektak® stylus profilers from Bruker. Film birefringence Δn is derived from the equation: $R_0 = \Delta n \cdot d$.

The FIG. 1 indicates the wavelength dispersion of the birefringence for examples 1 to 13 as compared to examples R2.

Example 17

General Procedure for LC-Coated Film Preparation on Photolalignment Layer from the Compound 1 to 13

Preparation of an Orientation Layer using Photoalignment Materials

A glass substrate was spin-coated with a photoalignment composition (2% solid content of photoaligning polymer in cyclopentanone as described in the application example on page 40 of patent publication WO2012/085048). The film was dried at 80° C. for 30 s and the resulting film thickness was about 100 nm. Then the film was exposed to aligning light, which was collimated and linearly polarized UV (LPUV) light (280-320 nm) with 500 mJ/cm$^2$. The plane of polarization was 0° with regard to a reference edge on the substrate.

Preparation of LC Formulation

A 15.0 w % solution of LC is prepared by mixing 14.63 w % of LC, 0.075 w % of inhibitor 2,6-di-tert-butyl-4-methylphenol (to prevent premature polymerisation), 0.30 w % of photoinitiator Irgacure 369 in cyclohexanone and stirred thoroughly till the solid is completely dissolved at room temperature. The coating liquid was applied onto a glass plate with the above orientation layer to form a liquid crystal film by spin coating. After drying the film for a time and a temperature shown in Table 3, the film sample is cooled down to room temperature and then photo-polymerised by irradiation with UV light using a Mercury lamp under $N_2$ atmosphere to fix the orientation state of the liquid crystal for approximately 2 min at a temperature described in Table 3.

TABLE 3

| Compounds | Time (mn) | Alignment temperature (° C.) | Curing Temperature (° C.) |
|---|---|---|---|
| 1 | 2 | 120 | 120 |
| 2 | 5 | 105 | 25 |
| 4 | 2 | 180 | 25 |
| 5 | 2 | 78 | 25 |
| 6 | 8 | 82 | 25 |
| 7 | 2 | 140 | 25 |
| 8 | 5 | 115 | 115 |
| 9 | 5 | 145 | 25 |
| 10 | 2 | 110 | 25 |

Example 18

Figure 2:
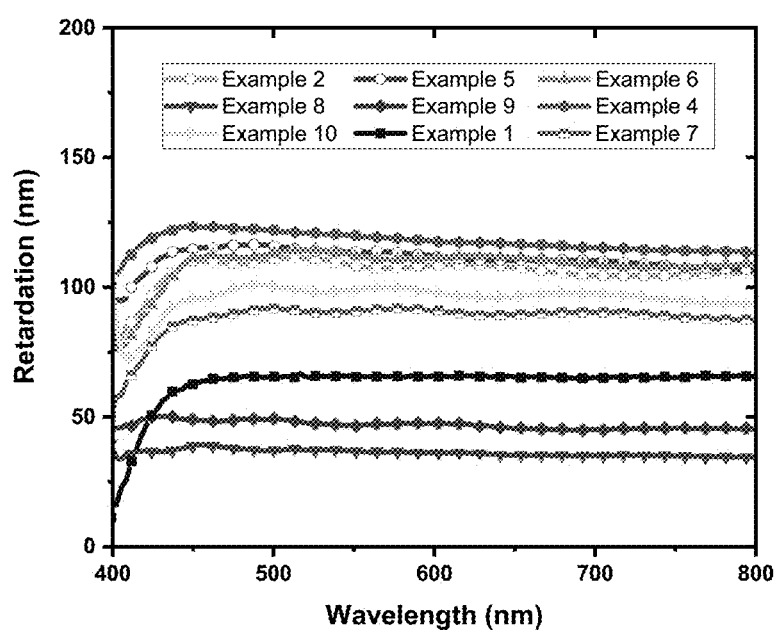
FIG. 2 shows the wavelength dispersion of LCPs films aligning on substrates coated with a photoaligning composition.

The retardation of the films made in example 17 was measured by Ellipsometry. The FIG. 2 indicates the retardation dispersion of the films made in example 17.

The results described above showed that liquid crystal film was produced with a retardation that increases in association with an increase of the wavelength in the visible light region.

The invention claimed is:

1. An anisotropic compound of formula (I)

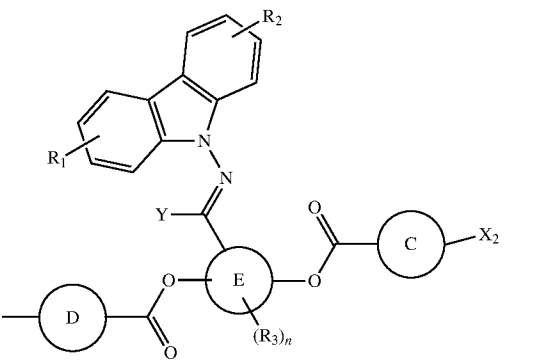

(I)

wherein $R_1$, $R_2$ and $R_3$ are independently from each other selected from the group consisting of hydrogen, $C_1$-$C_{12}$ straight alkyl chain, $C_3$-$C_{12}$ branched alkyl chain, $C_3$-$C_{12}$ alkenyl, $C_1$-$C_{12}$ alkoxy, $C_3$-$C_{12}$ alkenyloxy —$(CH_2)_m$—, —$C(CH_3)_3$, $NO_2$, CN, COR, —COOR, —OCOR, —CONR'R, —NR'COR, OCOOR, —OCONR'R, —NR'COOR, —F, —Cl, —$CF_3$ and —$OCF_3$;

in which m is an integer between 0 and 12;

R is selected from the group consisting of hydrogen, an $C_{1-18}$ alkyl group, an $C_{3-18}$ alkenyl group, $(CH_2)_p$—C—$(CF_3)_3$, CN, and unsubstituted or substituted phenyl ring, wherein the substituent of the phenyl ring is selected from the group consisting of $C_1$-$C_6$ straight alkyl chain, $C_3$-$C_6$ branched alkyl chain, $C_1$-$C_6$ alkoxy, —C—$(CH_3)_3$, halogen, —$CF_3$, $NO_2$, CN, COR''', —COOR''', —OCOR''', —CONR''R''', —NR''COR''', OCOOR''', —OCONR''R''', —NR''COOR''', —F, —Cl, —$CF_3$ and —$OCF_3$ in which R'' is selected from the group consisting of hydrogen, a lower alkyl group and a lower alkenyl group;

R''' is selected from the group consisting of hydrogen, an $C_{1-18}$ alkyl group and an $C_{3-18}$ alkenyl group;

p is an integer between 0 and 12;

R' is selected from the group consisting of hydrogen, lower alkyl, lower alkenyl and lower alkoxy;

n is 0, 1, 2 or 3;

Y is selected from the group consisting of H, or substituted or unsubstituted alkyl group having 1 to 12 carbon atoms;

rings C and D are independently from each other selected from the group consisting of phenyl, biphenyl, naphthyl, cycloalkyl, bicycloalkyl,

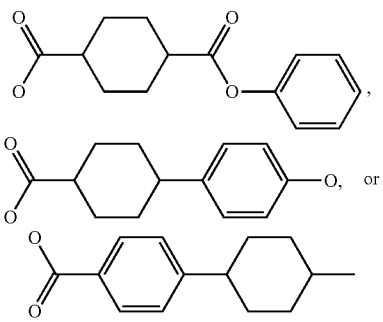

with the proviso that at least one of rings C or D is an aromatic ring;

ring E is selected from the group consisting of phenyl, biphenyl and naphthyl $X_1$ and $X_2$ are independently from each other selected from the group consisting of hydrogen, $C_1$-$C_{12}$ substituted or unsubstituted straight alkyl chain, $C_3$-$C_{12}$ substituted or unsubstituted branched alkyl chain, $C_3$-$C_{12}$ substituted or unsubstituted straight chain or branched alkenyl chain and $C_1$-$C_{12}$ alkoxy, wherein one or more carbon atoms may be replaced by —O—, —COO—, —OCO—, —OOC—, —O(CO)O—, —N—, —$NR^a$—, —CON—, wherein $R^a$ is a $C_1$-$C_{12}$ alkyl group; or $X_1$ and $X_2$ independently from each other are represented by the group of formula (II)

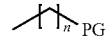 (formula II)

wherein n is an integer between 0 and 24, and wherein one or more C atoms may be replaced by —O—, —COO—, —OCO—, —OOC—, —O(CO)O—, —N—, —$NR^a$—, —CON—, wherein $R^a$ is a $C_1$-$C_{12}$ alkyl group; and PG represents a polymerisable group selected from the group consisting of $CH_2$=C(Ph)-, $CH_2$=CW—COO—, $CH_2$=CH—COO-Ph-, $CH_2$=CW—CO—NH—, $CH_2$=CH—O—, $CH_2$=CH—OOC—, Ph-CH=CH—, $CH_2$=CH-Ph-, $CH_2$=CH-Ph-O—, $R^b$-Ph-CH=CH—COO—, $R^b$—OOC—CH=CH-Ph-O— and 2-W-epoxyethyl; in which W represents H, Cl, Ph or a lower alkyl, $R^b$ represents a lower alkyl with the proviso that when $R^b$ is attached to a phenylene group (-Ph-) it may also represent hydrogen or a lower alkoxy.

2. The compound according to claim 1, wherein rings C and D are independently from each other selected from phenyl or cyclohexyl, with the proviso that at least one ring C or D is phenyl.

3. The compound according to claim 1, wherein rings C and D are both phenyl.

4. The compound according to claim 1, wherein ring E is a phenyl ring.

5. The compound according to claim 1, wherein the group of formula (II) representing $X_1$ and $X_2$ is independently from each other selected from the group consisting of

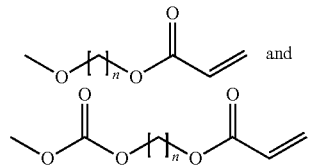

wherein n is an integer between 0 and 24 if rings C or D are aromatic rings or contain an aromatic ring; or the group of formula (II) representing $X_1$ and $X_2$ is independently from each other selected from the group consisting of, a hydrogen, $C_1$-$C_{12}$ substituted or unsubstituted straight alkyl chain, $C_3$-$C_{12}$ substituted or unsubstituted branched alkyl chain, $C_3$-$C_{12}$ substituted or unsubstituted straight chain or branched alkenyl chain and $C_1$-$C_{12}$ alkoxy, if rings C or D independently from each other are a cyclohexyl or contain a cyclohexyl, with the proviso that at least one ring C or D is an aromatic ring or a phenyl ring or contains an aromatic ring or a phenyl ring.

6. The compound according to claim 5, wherein rings C or D are independently from each other either phenyl or cyclohexyl.

7. The compound according to claim 1, wherein $R_1$, $R_2$ and $R_3$ are independently from each other selected from the group consisting of hydrogen, lower alkyl, lower alkenyl, lower alkoxy, lower alkenyloxy, —F and —$CF_3$.

8. The compound according to claim 1, wherein $R_1$, $R_2$ and $R_3$ are independently from each other selected from the group consisting of methyl, methoxy, F, $C(CH_3)_3$ and —$CF_3$.

9. An LCP mixture comprising the compound of formula (I) according to claim 1.

10. The LCP mixture according to claim 9 which is in cross-linked or polymerised form.

11. An LCP network comprising the compound according to claim 1.

12. A process for the manufacturing an optical film comprising an anisotropic compound according to claim 1, by exposing the anisotropic compound to aligning light.

13. An optical film comprising the anisotropic compound of formula (I) of claim 1.

14. A method of using the compound according to claim 1, comprising manufacturing an optical or an electro-optical device with the compound.

15. An optical or electro-optical device including the compound according to claim 1.

* * * * *